United States Patent
Schneeberger et al.

(10) Patent No.: US 7,335,510 B2
(45) Date of Patent: Feb. 26, 2008

(54) MODULATING PLANT NITROGEN LEVELS

(75) Inventors: Richard Schneeberger, Van Nuys, CA (US); Emilio Margolles-Clark, North Port, FL (US); Joon-Hyun Park, Oak Park, CA (US); Boris Jankowski, Santa Monica, CA (US); Steven Craig Bobzin, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/292,951

(22) Filed: Dec. 2, 2005

(65) Prior Publication Data

US 2006/0137034 A1   Jun. 22, 2006

Related U.S. Application Data

(60) Provisional application No. 60/705,119, filed on Aug. 2, 2005, provisional application No. 60/637,311, filed on Dec. 16, 2004.

(51) Int. Cl.
*A01H 5/00* (2006.01)
*A01H 1/00* (2006.01)
*C12N 15/82* (2006.01)
*C12N 15/87* (2006.01)

(52) U.S. Cl. .................. 435/468; 435/419; 800/278; 800/295

(58) Field of Classification Search .......... None
See application file for complete search history.

(56) References Cited

U.S. PATENT DOCUMENTS

| | | | |
|---|---|---|---|
| 4,987,071 A | 1/1991 | Cech et al. | |
| 5,204,253 A | 4/1993 | Sanford et al. | |
| 5,254,678 A | 10/1993 | Haseloff et al. | |
| 5,538,880 A | 7/1996 | Lundquist et al. | |
| 5,998,700 A | 12/1999 | Lightfoot et al. | |
| 6,013,863 A | 1/2000 | Lundquist et al. | |
| 6,329,571 B1 | 12/2001 | Hiei | |
| 6,423,885 B1 | 7/2002 | Waterhouse et al. | |
| 6,906,244 B2 | 6/2005 | Fischer et al. | |
| 2003/0233670 A1 | 12/2003 | Edgerton et al. | |
| 2005/0108791 A1 | 5/2005 | Edgerton | |
| 2006/0041952 A1 | 2/2006 | Cook et al. | |

FOREIGN PATENT DOCUMENTS

| | | |
|---|---|---|
| JP | 2004 121047 | 4/2004 |
| WO | 99/32619 | 7/1999 |
| WO | 00/31281 | 6/2000 |
| WO | 01/18191 | 3/2001 |
| WO | 01/35725 | 5/2001 |
| WO | 01/75164 | 10/2001 |
| WO | 02/10210 | 2/2002 |
| WO | 02/15675 | 2/2002 |
| WO | 02/16655 | 2/2002 |
| WO | WO 0210210 A2 * | 2/2002 |
| WO | 02/46449 | 6/2002 |
| WO | 02/081714 | 10/2002 |
| WO | 03/013227 | 2/2003 |
| WO | 03/095654 | 11/2003 |

OTHER PUBLICATIONS

Keskin et al. (Protein Science, 13: 1043-1055, 2004).*
Guo et al. (PNAS, 101: 9205-9210, 2004).*
Thornton et al. (Nature structural Biology, structural genomics supplement, Nov. 2000).*
Town et al. (NCBI, GenBank Accession No. NM_121195, pp. 1-2, Published Jan. 30, 2002).*
GenBank No. U93215, dated Feb. 27, 2002.
GenBank No. AF129516, dated Apr. 6, 1999.
GenBank No. AF096096, dated Jan. 25, 1999.
GenBank No. L05934, dated Oct. 22, 1993.
GenBank No. AL163815.1 dated Nov. 14, 2006.
GenBank NO. Q9LPV5, dated Mar. 1, 2004.
GenBank No. CAB87717, dated Nov. 14, 2006.
GenBank No. NP 196718, dated Jun. 9, 2006.
Abler, "Isolation and characterization of a genomic sequence encoding the maize *Cat3* catalase gene" *Plant Mol. Biol*, 22:10131-1038 (1993).
Apuya et al. "RASPBERRY3 Gene Encodes a Novel Protein Important for Embryo Development," *Plant Physiology*, 129(2):691-705 (2002).
Baerson et al., "Developmental regulation of an acyl carrier protein gene promoter in vegetative and reproductive tissues" *Plant Mol Biol.*, 22(2):255-267 (1993).
Bateman et al., "Pfam 3.1: 1313 multiple alignments and profile HMMs match the majority of proteins" *Nucl. Acids Res*. 27:260-262 (1999).
Baud, S.; Boutin, J.-P.; Miquel, M.; Lepiniec, L.; Rochat, C. An integrated overview of seed development in *Arabidopsis thaliana* ecotype WS, *Plant Physiol. Biochem*. 40 (2002) 151-160.
Bechtold et al., "*In planta* Agrobacterium mediated gene transfer by infiltration of adult *Arabidopsis thaliana* plants" *C.R. Acad. Sci. Paris*, 316:1194-1199 (1993).
Bustos, et al., "Regulation of B-Glucuronidase Expression in Transgenic Tobacco Plants by an A/T—Rich, cis-Acting Sequence Found Upstream of a French Bean -Phaseolin Gene" *Plant Cell*, 1:839-854 (1989).
Cerdan et al., "A 146 bp fragment of the tobacco *Lhcb1* *2 promoter confers very-low-influence, low-influence and high-irradiance responses of phytochrome to a minimal CaMV CaMV 35S promoter" *Plant Mol. Biol*. 33:245-255 (1997).

(Continued)

*Primary Examiner*—Phuong T. Bui
*Assistant Examiner*—Vinod Kumar
(74) *Attorney, Agent, or Firm*—Fish & Richardson P.C.

(57) ABSTRACT

Methods and materials for modulating (e.g., increasing or decreasing) nitrogen levels in plants are disclosed. For example, nucleic acids encoding nitrogen-modulating polypeptides are disclosed as well as methods for using such nucleic acids to transform plant cells. Plants and plant products having increased nitrogen levels are also disclosed.

15 Claims, 7 Drawing Sheets

OTHER PUBLICATIONS

Chen et al., "Functional analysis of regulatory elements in a plant embryo-specific gene" *Proc Natl Acad Sci USA*, 83:8560-8564 (1986).

Chenna, et al. "Multiple sequence alignment with the Clustal series of programs" *Nucleic Acids Res.*, 31 (13):3497-500 (2003).

Chichkova et al., "Transgenic tobacco plants that overexpress alfalfa (NADH-glutamate synthase have higher carbon and nitrogen content" *Journal of Experimental Botany*, 52(364):2079-2087 (2001).

Conceicao et al., "a cotyledon region is responsible for the different spatial expression patterns of *Arabidopsis* 2S albumin genes" *The Plant Journal*, 5:493-505 (1994).

Conkling et al., "Isolation of transcriptionally regulated root-specific genes from tobacco" *Plant Physiol.*, 93:1203-1211 (1990).

de Feyter and Gaudron, Methods in Molecular Biology, vol. 74, Chapter 43, "Expressing Ribozymes in Plants", Edited by Turner, P.C, *Humana Press Inc.*, Totowa, NJ.

Dietrich et al., "AtPTR1, a plasma membrane peptide transporter expressed during seed germination and in vascular tissue of *Arabidopsis" Plant Journal*, 40(4):488-499 (2004).

Ezeagu, I.E.; Petzke, J.K.; Metges, C.C.; Akinsoyinu, A.O.; Ologhobo, A.D. Seed protein contents and nitrogen-to-protein conversion factors for some uncultivated tropical plant seeds, *Food Chemistry*, 78 (2002) 105-109.

Fejes et al., "A 268 bp upstream sequence mediates the circadian clock-regulated transcription of the wheat Cab-1 gene in transgenic plants" *Plant Mol. Biol.*, 15:921-932 (1990).

Foyer et al., "Adaptations of photosynthetic electron transport, carbon assimilation, and carbon partitioning in transgenic *Nicotina plumbaginifolia* plants to change in nitrate reductase activity". *Plant Physiology*, 104(1):171-178 (1994).

Fraisier et al., *Plant Journal*, 23(4):489-496 (2000).

Fromm et al., "An octopine synthase enhancer directs tissue-specific expression and binds ASF-1, a factor from tobacco nuclear extracts" *The Plant Cell*, 1:977-984 (1989).

Green, et al., "Binding site requirements for pea nuclear protein factor GT-1 correlate with sequences required for light-dependent transcriptional activation of the *rbcS-3A* gene" *EMBO J.* 7, 4035-4044 (1988).

Heath, J.D.; Weldon R.; Monnot, C.; Meinke, D.W. Analysis of storage proteins in normal and aborted seeds from embryo-lethal mutants of *Arabidosis thaliana*, Planta 169 (1986) 304-312.

Hong et al., "Promoter sequences from two different *Brassica napus* tapetal oleosin-like genes direct tapetal expression of B-glucuronidase in transgenic *Brassica* plants" *Plant Mol Biol.*, 34(3):549-555 (1997).

Huang et al., "Cloning and functional characterization of an *Arabidopsis* nitrate transporter gene that encodes a constitutive component of low-affinity uptake" *Plant Cell*, 11(8):1381-1392 (1999).

Hwang et al., "Aleurone- and embryo-specific expression of the β-glucuronidase gene controlled by the barley *Chi26* and *Ltp1* promoters in transgenic rice" *Plant Cell Rep.*, (2001) 20:647-654.

Hyrup et al., "Peptide nucleic acids (PNA): Synthesis, properties and potential applications" *Bioorganic Med. Chem.*, 4: 5-23 (1996).

Jordano, et al., "A sunflower helianthinin gene upstream sequence ensemble contains an enhancer and sites of nuclear protein interaction" *Plant Cell*, 1:855-866 (1989).

Koch et al., "Reduced amino acid content in transgenic potato tubers due to antisense inhibition of the leaf H+/amino acid symporter StAAP1" *Plant Journal*, 33(2):211-220 (2003).

Lam et al., "Site-specific mutations alter in vitro factor binding and change promoter expression pattern in transgenic plants" *Proc. Natl. Acad. Sci. USA*, 86:7890-7894 (1989).

Li et al., "Oil content of arabidopsis seeds: The influence of seen anatomy, light and plant-to-plant variation" Phytochemistry, 2006, 67:904-915.

Luan et al., "A rice *cab* gene promoter contains separate *cis*-Acting elements that regulate expression in dicot and monocot plants" *Plant Cell*, 4:971-981 (1992).

Lubberstedt et al., "Promoters from genes for plastid proteins possess regions with different sensitivities toward red and blue light" *Plant Physiol.*, 104:997-1006 (1994).

Matsuoka et al., "Tissue-specific light-regulated expression directed by the promoter of a $C_4$ gene, maize pyruvaté, orthophosphate dikinase, in a $C_3$ plant, rice" *Proc Natl Acad. Sci USA*, 90:9586-9590 (1993).

McClure et al., "Transcription, Organization, and Sequence of an Auxin-Regulated Gene Cluster in Soybean" *Plant Cell*, 1:229-239 (1989).

Meier, et al., "Elicitor-inducible and constitutive in Vivo DNA footprints indicate novel *cis*-acting elements in the promoter of a parsley gene encoding pathogenesis-related protein 1" *Plant Cell*, 3, 309-316 (1991).

Perriman, et al., "Effective ribozyme delivery in plant cells" *Proc. Natl. Acad. Sci. USA*, 92(13):6175-6179 (1995).

Rhee, K.C. "Determination of Total Nitrogen In Handbook of Food Analytical Chemistry—Water, Proteins, Enzymes, Lipids, and Carbohydrates. (R. Wrolstad, et. al, ed.)" *John Wiley and Sons, Inc.*, 2005, pp. 105.

Riggs et al., "Cotyledon nuclear proteins bind to DNA fragments harboring regulatory elements of phytohemagglutinin genes" *The Plant Cell*, 1(6):609-621 (1989).

Rivera et al., "Genomic evidence for two functionally distict gene classes" *Proc. Natl. Acad. Sci. USA*, 95:6239-6244 (1998).

Sheridan et al., "the *mac1* gene: Controlling the commitment to the meiotic pathway in maize" *Genetics*, 142:1009-1020 (1996).

Slocombe et al., "Temporal and tissue-specific regulation of a *Brassica napus* stearoyl-acyl carrier protein desaturase gene" *Plant Physiol*, 104(4):167-176 (1994).

Sonnhammer et al., "Pfam: multiple sequence alignments and HMM-profiles of protein domains" *Nucl. Acids Res.*, 26: 320-322 (1998).

Sonnhammer et al., "Pfam: A comprehensive database of protein domain families based on seed alignments", *Proteins*, 28:405-420 (1997).

Summerton and Weller, "Morpholino antisense oligomers: Design, preparation, and properties", *Antisense Nucleic Acid Drug Dev.*, 7:187-195 (1997).

Truernit et al., "The promoter of the *Arabidopsis thaliana* SUC2 sucrose-H+ symporter gene directs expression of B-glucuronidase in the phloem: evidence for phloem loading and unloading by SUC2" *Planta*, 196:564-570 (1995).

Tuskan et al., "The genome of black cottonwood, *Populus trichocarpa" Science*, 2006, 313(5793):1596-604.

Urao et al., "Molecular cloning and characterization of a gene that encodes a MYC-related protein in *Arabidopsis" Plant Mol. Biol.*, 32:571-57 (1996).

Weber et al., "Interaction of cytosolic and plastidic nitrogen metabolism in plants" *Journal of Experimental Botany*, 53(370):865-874 (2002).

Yamamoto et al., "The promoter of a pine photosynthetic gene allows expression of a B-glucuronidase reporter gene in transgenic rice plants in a light-independent but tissue-specific manner" *Plant Cell Physiol.* 35:773-778 (1994).

Yanagisawa et al., "Metabolic engineering with Dof1 transcription factor in plants: Improved nitrogen assimilation and growth under low-nitrogen conditions" *PNAS*, 101(20):7833-7838 (2004).

Zhang, et al., "DNA sequences that activate isocitrate lyase gene expression during late embryogenesis and during postgerminative growth" *Plant Physiology* 110: 1069-1079 (1996).

Zheng et al., "SPK1 is an essential S-phase-specific gene of *Saccharomyces cerevisiae* that encodes a nuclear serine/threonin/tyrosine kinase" *Mol. Cell Biol.* 13:5829-5842 (1993).

GenBank Accession No. BAC43284, dated Feb. 14, 2004.

Hill et al. "Carbon supply for storage-product synthesis in developing seeds of oilseed rape" *Biochemical Society Transactions*, 28(6):667-669 (2000).

Katavic et al "Utility of the *Arabidopsis* FAE1 and yeast SLC1-1 genes for improvements in erucic acid and oil content in rapeseed" *Biochemical Society Transactions*, 28(6):935-937 (2000).

Singh et al. "Transgenic expression of a delta 12-epoxygenase gene in *Arabidopsis* seeds inhibits accumulation of linoleic acid" *Planta*, 212(5-6):872-879 (2001).

Tomlinson et al. "Evidence that the hexose-to sucrose ration does not control the switch to storage product accumulation in oilseeds: analysis of tobacco seed development and effects of overexpressing apoplastic invertase" *Journal of Experimental Botany*, 55(406):2291-2303 (2004).

* cited by examiner

Figure 1

| | | | | | |
|---|---|---|---|---|---|
| SEQ-ID-NO-17:gi\|33411520 | MSNCTLPETQ | E--------- | ---------- | ---------- | ----KLTL | 35 |
| SEQ-ID-NO-16:CeresClone:352232 | -MDAQDDDER | PLIIHRLPLL | ---------- | QDESTSGFTS | PDAWDFKGRP AERSKTGGWT | 49 |
| SEQ-ID-NO-18:gi\|31429847 | --MAAIEEER | PLL----PLQ | ---------- | SQDVGSEYTR | DGTVDLRNQP ARKQRTGNWR | 44 |
| SEQ-ID-NO-14:gi\|50059161 | MDSTDQFDNS | PLLDG---DGS | ---------- | SQENTTEYTG | DGSVDINKEP ALKHSTGNWR | 48 |
| SEQ-ID-NO-12:gi\|56784523 | -MEGVES--- | ---------- | ---------- | ----------CN | GRHADADDRR ASRKHTGNWK | 28 |
| SEQ-ID-NO-11:gi\|6635838 | --MGSLEEER | SLLED--GLI | ---------- | QDETNGLYTG | DGSVDITLGKP TSKKDRRTTW | 46 |
| SEQ-ID-NO-9:gi\|4102839 | --MKYLFSKN | G-----GLL | ---------- | EDENSGLYTR | DGSVDIKGNP VLKQSTGNWX | 42 |
| SEQ-ID-NO-10:gi\|31088360 | --MGSVEDDS | SRLEE--ALI | ---------- | QDEESKLYTG | DGSVDFKGRP VLKSETGNWR | 46 |
| Lead-SEQ-ID-NO-4:Clone:117581 | ---MEEKD-- | ---------- | ---------- | ---VYTQ | DGTVDIKGNP VLKKNTGNWK | 29 |
| SEQ-ID-NO-6:gi\|2655098 | ---MGEVAAE | ---------- | ---------- | ----MYTQ | DGTVDIKGNP ALKKDTGNWR | 31 |
| SEQ-ID-NO-5:CeresClone:328378 | ---MGEVED- | ---------- | ---------- | ----MYTQ | DGTVDMKGNP AVKKGTGNWR | 30 |
| SEQ-ID-NO-7:gi\|34895718 | ---MGEVAED | ---------- | ---------- | ----YTQ | DGTVDVKGNP ATKKNTGNWR | 31 |

Consensus     ---M-EVE-E-  ----------  ----------  ---E----MYTQ  DG-VDI KG-P  ALKK-TGNWR    50

| | | | | | |
|---|---|---|---|---|---|
| SEQ-ID-NO-17:gi\|33411520 | AAAMLGGEA | CERLTTLGIA | ---------- | VNLVT-YLTG | TMHLGNATSA NTVTNFLGTS | 84 |
| SEQ-ID-NO-16:CeresClone:352232 | ACFFILGAEF | AECVAFFA-S | ---------- | KNLVT-YLTG | VLHESNVDAA TTVSTWIGTS | 98 |
| SEQ-ID-NO-18:gi\|31429847 | ACFLILGAVEF | CENMTYFVLG | ---------- | RNLVT-FLTT | VLHESKYDAA RNVSAMVGAC | 93 |
| SEQ-ID-NO-14:gi\|50059161 | ASFLILVCSF | CCYLAYSSI | ---------- | KNLVS-YLTK | VLHETNLDAA RHVATMQGTS | 97 |
| SEQ-ID-NO-12:gi\|56784523 | ASAFILVNNF | MQYTAYFGVS | ---------- | TNLVN-YLKY | RLHEGSKSAA NDVTNWQGTG | 77 |
| SEQ-ID-NO-11:gi\|6635838 | ACPFILGNEC | CERLAYYGIA | ---------- | ANLVT-YLTK | KLHEGNVSAA RNVTTWSGTC | 95 |
| SEQ-ID-NO-9:gi\|4102839 | ACPFILGNEC | CERLAYYGIA | ---------- | TNLVT-YLTH | KLHEGNVSAA RNVTTWQGTC | 91 |
| SEQ-ID-NO-10:gi\|31088360 | ACPFILGNEC | CERLAYYGIA | ---------- | TNLVKPLLA | KLHEGNVSAA RNVTTWQGTC | 96 |
| Lead-SEQ-ID-NO-4:Clone:117581 | ACRFILGNEC | CERLAYYGMG | ---------- | TNLVN-YLES | RLNQGNATAA NNVTNWSGTC | 78 |
| SEQ-ID-NO-6:gi\|2655098 | ACPYILANEC | CERLAYYGMS | ---------- | TNLVN-FMKD | RMGMANAAAA NNVTNWQGTC | 80 |
| SEQ-ID-NO-5:CeresClone:328378 | ACPYILANEC | CERLAYYGMS | ---------- | TNLVN-YMKT | RLGQVNSVAS NNVTNWQGTC | 79 |
| SEQ-ID-NO-7:gi\|34895718 | ACPYILANEC | CERLAYYGMS | ---------- | TNLVN-YMKT | RLGQESAIAA NNVTNWSGTC | 80 |

Consensus     ACPFILGNEC  CERLAYYGIS  ----------  TNLV--YLT-  RLHEGNVSAA  NNVTNW-GTC    100

Figure 1 (Continued)

| | | | | | |
|---|---|---|---|---|---|
|SEQ-ID-NO-17-gi\|334111520|FML CLLGGFV|ADTFLGRYLT|AIFATFQAM|GVTLLTISLT|PSLRPPKC-|133|
|SEQ-ID-NO-16-CeresClone:352232|FETPLVGAFL|ADTFWGRYWT|AFLSVYYT|GMTVLTASAL|LPLLMGASY-|147|
|SEQ-ID-NO-18-gi\|314429847|FLTPVVGAFL|ADTYWGRYWT|VVFLPVYIT|GMLIVTVSAS|LPMFLTSSE-|142|
|SEQ-ID-NO-14-gi\|50059161|YLAPLVGAFV|ADSYLGKYRT|ALACKIFII|GMMMLLSAA|LQLSAGPH-|146|
|SEQ-ID-NO-12-gi\|56784523|STPLVAYL|ADAFLGRYWT|LFMAISVL|GYGVLAASAA|APALLHGGA|126|
|SEQ-ID-NO-11-gi\|66355838|YLTPLIGAVL|ADAYWGRYWT|AIFSTIYFI|GMCTLTISAS|VPALKPPQC-|144|
|SEQ-ID-NO-9-gi\|41102839|YLAPLIGAVL|ADSYWGRYWT|ATFSMIYFI|GMGTLTLSAS|VPAFKPPQC-|140|
|SEQ-ID-NO-10-gi\|310088360|YITPLIGAFI|ADAYLGRYWT|AIFSMIYFI|GMGTLTLSAS|PALKPAEC-|145|
|Lead-SEQ-ID-NO-4-Clone:117581|YITPLIGAFL|ADAYLGRFWT|ATFVFIYVS|GMTLLTLSAS|VPGLKPGNC-|127|
|SEQ-ID-NO-6-gi\|2655098|YITPLIGAFL|ADAYMGRFWT|ASFMIYIF|GLGLLTMATS|VHGLVPACA-|129|
|SEQ-ID-NO-5-CeresClone:328378|YITPLIGAFF|ADAYMGRFWT|AIFMIYIF|GLALLTMASS|VKGLVPTSCG|129|
|SEQ-ID-NO-7-gi\|34895718|YITPLLGAFL|ADAYMGRFWT|ASFMIYIL|GLALLTMASS|VKGLVPAC--|128|
| | | | | | |
|Consensus|YITPLIGAFL|ADAYLGRYWT|IAIFM-IYII|GM-LLTLSAS|VP-LVP--C-|150|
| | | | | | |
|SEQ-ID-NO-17-gi\|334111520|TSDTSTPCP|ASCKQLMVLY|ALYLTALGT|GGLKSSVSGF|GSDQFDESDK|183|
|SEQ-ID-NO-16-CeresClone:352232|SRSA------|----HRLSAY|LGLYLAALGT|GGIKPCVCAL|GADQFDASDP|187|
|SEQ-ID-NO-18-gi\|314429847|HCNV------|----HRSVVY|LGLYLAALGS|GAMKPCTTS|GADQFDSTDL|182|
|SEQ-ID-NO-14-gi\|50059161|AWTV--WVH|LVSSQYTIFL|GLYMVGLGY|GAQRPCVTSF|GADQFDDTDY|193|
|SEQ-ID-NO-12-gi\|56784523|----------|----AAFY|AGLYLVALGS|GLVVMAPF|GAGQFDEADE|159|
|SEQ-ID-NO-11-gi\|66355838|VDSV------|ASPAQYGVFF|FGLYLIALRT|GGIKPCVSSF|GADQFDDTDS|191|
|SEQ-ID-NO-9-gi\|41102839|VGSV------|ASPAQYAIFF|FGLYLIALFF|GGIKPCVSSF|GADQFDDTDP|187|
|SEQ-ID-NO-10-gi\|310088360|LGAV------|ATPAQYAVFF|GLYLIALFF|GGIKPCVSSF|GADQFDDTDS|192|
|Lead-SEQ-ID-NO-4-Clone:117581|NADT------|-NSSQTAVFF|VALYMIALGT|GGIKPCVSSF|GADQFDENDE|173|
|SEQ-ID-NO-6-gi\|2655098|SKGV------|TPGQSAAVF|LALYLIALGT|GGIKPCVSSF|GADQFDEHDD|175|
|SEQ-ID-NO-5-CeresClone:328378|DKDV------|TDAQAAVF|VALYLIALGT|GGIKPCVSSF|GADQFDENDE|175|
|SEQ-ID-NO-7-gi\|34895718|DGGA------|TEAQTGVVF|LALYLIALGT|GGIKPCVSSF|GADQFDENDE|174|
| | | | | | |
|Consensus|---V--C-P|---AQ-AVFF|IGLYLIALGT|GGIKPCVSSF|GADQFDE-DE|200|

| SEQ ID | | | | | | |
|---|---|---|---|---|---|---|
| SEQ-ID-NO-17-gi\|33411520 | KSFQIPPASL | TAFFVGSILL | TVPVYDRLIV | PMARKALENP | QGLTPLQRMG | 428 |
| SEQ-ID-NO-16-CeresClone:352232 | -PFTVPPASL | STFDMSVMV | CIPIYDKALV | PLARRATGKE | RGLSQLQRLG | 431 |
| SEQ-ID-NO-18-gi\|314298847 | -SFAIPPASL | LITAVLSVLV | LVPVYERLIV | PLVKHFTGQD | KGFSHAQRIG | 424 |
| SEQ-ID-NO-14-gi\|50059161 | -SFEIPSASF | QCVDTITVIV | LVPIYERLIV | PVLRKFTGRA | NGITSPQRIG | 434 |
| SEQ-ID-NO-12-gi\|56784523 | -GFKVPAAVL | SVFDTLSVML | WVPLYDRAIV | PLARRVTGHD | RGFTQLARMG | 401 |
| SEQ-ID-NO-11-gi\|66635838 | -SFTIPPASL | SSFDVSVIF | WVPIYDRFIV | PIARKFTGKE | RGFSELQRMG | 432 |
| SEQ-ID-NO-9-gi\|4102839 | -SFKIPAASL | STFDTISVIV | WVPVYDKILV | PIARRFTGIE | RGFSELQRMG | 428 |
| SEQ-ID-NO-10-gi\|31088360 | -SFKIPAASL | STFDVSVIF | WVPVYDRFIV | PIARKFTGKE | RGFSELQRMG | 433 |
| Lead-SEQ-NO-4-Clone:117581 | KNFEIPSASL | SLFDTVSVLF | WVPVYDQFI- | PIARKFTGIE | RGFTQLQRMG | 415 |
| SEQ-ID-NO-6-gi\|2655098 | PKFKIPSASL | SIFDTLSVIA | WVPVYDRILV | PAVRSVTGRP | RGFTQLQRMG | 414 |
| SEQ-ID-NO-5-CeresClone:328378 | PRFKIPSATL | SMVDTISVIV | WVPVYDRAIV | PLVRSYTGRP | RGFTQLQRMG | 414 |
| SEQ-ID-NO-7-gi\|34895718 | PHFSLPAASL | SIFDTLSVIV | WVPVYDRLIV | PAVRAVTGRP | RGFTQLQRMG | 415 |
| Consensus | -SFKIP-ASL | SVFDTISVIV | WVPVYDR-IV | PLARKFTGRE | RGFTQLQRMG | 450 |

| SEQ ID | | | | | | |
|---|---|---|---|---|---|---|
| SEQ-ID-NO-17-gi\|334411520 | VGLVFSIFAM | VAAALTEVKR | LNIARSHGLT | DNP--TAELP | LSVFWLVPQF | 476 |
| SEQ-ID-NO-16-CeresClone:352232 | VGLALSVAGM | VYAALLEARR | LSLARA-AAG | GRP----P | MSIMWQAPAF | 474 |
| SEQ-ID-NO-18-gi\|314298847 | GLSLSMIMM | VYAALLEMKR | LAIVQSSGLA | DHN---VAAP | MSILWQTPAY | 471 |
| SEQ-ID-NO-14-gi\|50059161 | GLCFSMFSM | VSAALVEGNR | LQIAQAECLV | HRK---VAVP | MSIMWQGPQY | 481 |
| SEQ-ID-NO-12-gi\|56784523 | VGLVILTVAM | LVACTLEVAR | RRVLARHGLY | GDDCDGGYLP | LSIFWQVPQY | 451 |
| SEQ-ID-NO-11-gi\|66635838 | GLFLSVLCM | SAAAVVEMKR | LQLATELGLV | DKE---VAVP | SIFWQIPQY | 479 |
| SEQ-ID-NO-9-gi\|4102839 | GLFLSMLCM | SAAAIVEIRR | LQLARDLGLV | DEA---VSVP | SIFWQIPQY | 475 |
| SEQ-ID-NO-10-gi\|31088360 | GLFLSVLCM | SAAAIVEIKR | LQLAKELDLV | DKA---VPVP | LTIFLQIPQY | 480 |
| Lead-SEQ-NO-4-Clone:117581 | GLVVSIFAM | TAGVLEVVR | LDYVKTHNAY | DQK---Q-H | MSIFWQIPQY | 461 |
| SEQ-ID-NO-6-gi\|2655098 | GLVVSMFAM | LAAGVLELVR | LRTIAQHGLY | GEK---DVVP | SIFWQVPQY | 461 |
| SEQ-ID-NO-5-CeresClone:328378 | GLVVSIFSM | VAAGVLDIVR | LRAIARHGLY | GED---DIVP | SIFWQVPQY | 461 |
| SEQ-ID-NO-7-gi\|34895718 | GLVISVFSM | LAAGVLDVVR | LRAIARHGLY | GDK---DVVP | SIFWQVPQY | 462 |
| Consensus | IGLVIS-FAM | VAAAVLEVKR | L-I--R-HGL | -DE------VP | LSIFWQVPQY | 500 |

| SEQ ID | Sequence | Position |
|---|---|---|
| SEQ-ID-NO-17·gi\|33411520 | YKDKRLAEEG IELEEPEI CA HA---- ----- | 596 |
| SEQ-ID-NO-16·CeresClone:352232 | GSSNN STYSS ----- ----- ----- ----- | 584 |
| SEQ-ID-NO-18·gi\|31429847 | ENTAS ----- ----- ----- ----- ----- | 576 |
| SEQ-ID-NO-14·gi\|50059161 | CKKAS ----- ----- ----- ----- ----- | 586 |
| SEQ-ID-NO-12·gi\|56784523 | YKKT VD ----- ----- ----- ----- ----- | 557 |
| SEQ-ID-NO-11·gi\|6635838 | ----- ----- ----- ----- ----- ----- | 559 |
| SEQ-ID-NO-9·gi\|4102839 | SKKAS ----- ----- ----- ----- ----- | 580 |
| SEQ-ID-NO-10·gi\|31088360 | SKKAS ----- ----- ----- ----- ----- | 584 |
| Lead·SEQ-ID-NO-4·Clone:117581 | YKKAV GRAHK CCSLEPI VQT FGNKVS | 587 |
| SEQ-ID-NO-6·gi\|2655098 | YKKT AGDS ----- ----- PDAKG GAHDQ- | 579 |
| SEQ-ID-NO-5·CeresClone:328378 | YKKT ADDY ----- ----- PGAKG EHGTEH | 580 |
| SEQ-ID-NO-7·gi\|34895718 | YKKT ADS ----- ----- PDDKA EHAGAN | 580 |
| Consensus | YKK-S ----- ----- ----- ----- ----- | 626 |

SEQUENCE LISTING

```
<160> NUMBER OF SEQ ID NOS: 25

<210> SEQ ID NO 1
<211> LENGTH: 1446
<212> TYPE: DNA
<213> ORGANISM: Arabidopsis thaliana
<220> FEATURE:
<221> NAME/KEY: misc_feature
<222> LOCATION: (1)..(1446)
<223> OTHER INFORMATION: Ceres CDNA ID no. 2998984
<220> FEATURE:
<221> NAME/KEY: CDS
<222> LOCATION: (120)..(687)
<223> OTHER INFORMATION: Referenced by SEQ ID NO: 2

<400> SEQUENCE: 1
atggatcaag aagctcttct cgtcggaaga actcttctga agcgcggtat tccgaccatt      60
```

-continued

| | |
|---|---|
| cctttcattc tagcaagtca ggctttggag aaacttgcat attttggttt ggtaccgaac | 120 |
| atgatactct tcttgacggt ggaatacggc atgggaacag cggaagcggc caacatcctc | 180 |
| ttcctctggt ctgccgccac caatttcttc cctcttgttg gtgcttttat cgctgattct | 240 |
| tacaccggtc ggtttcctct gatcgggttt ggatcctcca tcagccttac gggaatggtt | 300 |
| ttgttatggc tgacaacaat aattcgacca gaatgcgata aattaacaaa cgtgtgccaa | 360 |
| cccaccacac tgctcaaaag tgttcttcta tattccttt tgccctcac cgccattggt | 420 |
| gccggcggcg ttagatcctc ctgcttagcc ttcgctgccg accagctcca acctaatcag | 480 |
| acatcacgtg tcaccacatc atccctagaa acgctcttca actggtacta cttctccgtc | 540 |
| atggtcgcat gctttctttc tcagtctttg ctcgtcttcg ttcagacaac gtatggttgg | 600 |
| cagatcggtt ttggagtttc tgtcgctgcc atggctctat cggtcgcttt gttcttcgcg | 660 |
| gcgtctccgt actatgtaag gtttcagaaa ccgacacgga actcaaggaa tccatggaag | 720 |
| ctatgtaggg tgcaacaagt agaagatctt aaatctctca tcaatgtcat accaatttgg | 780 |
| tcaacaggga tcatcttgtc acttgtcacg gcttgccaag tctccttcat agtccttcaa | 840 |
| gctaagacca tggatcgcca caccttcatt cagggtttcg agattcctcc aggctcttac | 900 |
| ggcattttct tggtcatctc cttttgctc ttccttggtc tttacgatct tgttatcgtc | 960 |
| ccattacttt cttgggctct aagagaaccc tttcgattgg gagttatggt gagaatgtgg | 1020 |
| gctgggtatg taatatcggt tttgtgcatc tccgctcttg cggctacgga gtacgcgagg | 1080 |
| agaaaaacag cgagagacga gagtggtacc aagttgtcgg cgatgtggct attaccgtac | 1140 |
| atgatattag gaggcattgc ggaagcactt aatacaatag cacagaacga gttcttctac | 1200 |
| tcagaacttc ccaaaaccat gtcaagcgtc gccaccacac tctccagtct caacatggcc | 1260 |
| gcagcaagcc tcatctcctc ctggatcatc accatcgttg acgttaccac ttacgggagc | 1320 |
| tgatcacag agaatataga cgagggacac ttggactatt actactgct cttggtggga | 1380 |
| ttatctttgc tgaatgtttt gtattttgtg tggtgtaaga aatcttatgg taaatgtagt | 1440 |
| atataa | 1446 |

<210> SEQ ID NO 2
<211> LENGTH: 505
<212> TYPE: PRT
<213> ORGANISM: Arabidopsis thaliana
<220> FEATURE:
<221> NAME/KEY: misc_feature
<222> LOCATION: (50)..(443)
<223> OTHER INFORMATION: Pfam Name: PTR2; Pfam Description: POT family

<400> SEQUENCE: 2

```
Met Ile Leu Phe Leu Thr Val Glu Tyr Gly Met Gly Thr Ala Glu Ala
1               5                  10                  15

Ala Asn Ile Leu Phe Leu Trp Ser Ala Ala Thr Asn Phe Phe Pro Leu
            20                  25                  30

Val Gly Ala Phe Ile Ala Asp Ser Tyr Thr Gly Arg Phe Pro Leu Thr
        35                  40                  45

Gly Phe Gly Ser Ser Ile Ser Leu Thr Gly Met Val Leu Leu Trp Leu
    50                  55                  60

Thr Thr Ile Asn Arg Pro Glu Cys Asp Lys Leu Thr Asn Val Cys Gln
65                  70                  75                  80

Pro Thr Thr Leu Leu Lys Ser Val Leu Leu Tyr Ser Phe Phe Ala Leu
                85                  90                  95

Thr Ala Ile Gly Ala Gly Gly Val Arg Ser Ser Cys Leu Ala Phe Ala
```

```
            100                 105                 110
Ala Asp Gln Leu Gln Pro Asn Gln Lys Ser Arg Val Thr Thr Ser Ser
            115                 120                 125

Val Glu Thr Leu Phe Asn Trp Tyr Tyr Phe Ser Val Met Val Ala Cys
        130                 135                 140

Phe Leu Ser Gln Ser Leu Leu Val Phe Val Gln Thr Thr Tyr Gly Trp
145                 150                 155                 160

Gln Ile Gly Phe Gly Val Ser Val Ala Ala Met Ala Leu Ser Val Ala
                165                 170                 175

Leu Phe Phe Ala Ala Ser Pro Tyr Tyr Val Arg Phe Lys Cys Glu Ser
            180                 185                 190

Gly Leu Val Thr Gly Leu Phe Gln Val Leu Ala Ala Phe Arg Asn
        195                 200                 205

Arg His Val Asp Leu Ser Ser Glu His Ile Ile Ser Tyr His His
        210                 215                 220

Glu Thr Gly Ser Ser Phe Ser Ile Pro Ser Gln Lys Leu Arg Tyr Leu
225                 230                 235                 240

Asn Lys Ala Cys Val Thr Asn Ser Lys Gln Asp Leu Ala Leu Thr
                245                 250                 255

Gly Asn Ser Arg Asn Pro Trp Lys Leu Cys Arg Val Gln Gln Val Glu
            260                 265                 270

Asp Leu Lys Ser Leu Ile Asn Val Ile Pro Ile Trp Ser Thr Gly Ile
        275                 280                 285

Ile Leu Ser Leu Val Thr Ala Cys Gln Val Ser Phe Ile Val Leu Gln
290                 295                 300

Ala Lys Thr Met Asp Arg His Thr Phe Ile Gln Gly Phe Glu Ile Pro
305                 310                 315                 320

Pro Gly Ser Tyr Gly Ile Phe Leu Val Ile Ser Phe Leu Leu Phe Leu
                325                 330                 335

Gly Leu Tyr Asp Leu Val Ile Val Pro Leu Leu Ser Trp Ala Leu Arg
            340                 345                 350

Ala Pro Phe Arg Leu Gly Val Met Val Arg Met Trp Ala Gly Tyr Val
        355                 360                 365

Ile Ser Val Leu Cys Ile Ser Ala Leu Ala Ala Thr Glu Tyr Ala Arg
370                 375                 380

Arg Lys Thr Ala Arg Asp Glu Ser Gly Thr Lys Leu Ser Ala Met Trp
385                 390                 395                 400

Leu Leu Pro Tyr Met Ile Leu Gly Gly Ile Ala Glu Ala Leu Asn Thr
                405                 410                 415

Ile Ala Gln Asn Glu Phe Phe Tyr Ser Glu Leu Pro Lys Thr Met Ser
            420                 425                 430

Ser Val Ala Thr Thr Leu Ser Ser Leu Asn Met Ala Ala Ala Ser Leu
        435                 440                 445

Ile Ser Ser Trp Ile Ile Thr Ile Val Asp Val Thr Thr Tyr Gly Ser
450                 455                 460

Trp Ile Thr Glu Asn Ile Asp Glu Gly His Leu Asp Tyr Tyr Tyr Trp
465                 470                 475                 480

Leu Leu Val Gly Leu Ser Leu Leu Asn Val Leu Tyr Phe Val Trp Cys
                485                 490                 495

Lys Lys Ser Tyr Gly Lys Cys Ser Ile
            500                 505

<210> SEQ ID NO 3
```

<211> LENGTH: 1764
<212> TYPE: DNA
<213> ORGANISM: Arabidopsis thaliana
<220> FEATURE:
<221> NAME/KEY: misc_feature
<222> LOCATION: (1)..(1764)
<223> OTHER INFORMATION: Ceres CLONE ID no. 117581
<220> FEATURE:
<221> NAME/KEY: CDS
<222> LOCATION: (1)..(1761)
<223> OTHER INFORMATION: Referenced by SEQ ID NO: 4

<400> SEQUENCE: 3

| | | | | | |
|---|---|---|---|---|---|
| atggaagaaa | aagatgtgta | tacgcaagat | ggaactgttg | atattcacaa | caatcctgca | 60 |
| aacaaggaga | aaaccggaaa | ttggaaagct | tgccgcttca | ttctcggaaa | tgagtgctgt | 120 |
| gaaagattgg | cctactatgg | catgggcact | aaccttgtga | attatcttga | gagccgtctg | 180 |
| aatcaaggca | atgctacggc | tgcaaataac | gtcacgaatt | ggtctggaac | atgttatata | 240 |
| actcctttga | ttggagcctt | tatagctgat | gcttaccttg | acgatattg | gactattgca | 300 |
| acttttgttt | tcatctatgt | ctccggtatg | actctttga | cattatcagc | ttcagttcct | 360 |
| ggacttaaac | caggtaactg | caatgctgat | acttgtcatc | caaattctag | tcagactgct | 420 |
| gttttctttg | tcgcgcttta | tatgattgct | cttggaactg | gcggtataaa | gccgtgtgtt | 480 |
| tcgtcctttg | gagctgatca | gtttgatgag | aatgatgaga | atgagaagat | caagaaaagt | 540 |
| tctttcttca | actggtttta | cttctccatt | aatgttggag | ctctcattgc | tgcaactgtt | 600 |
| ctcgtctgga | tacaaatgaa | tgttggttgg | ggatgggggtt | tcggtgttcc | aacagtcgcg | 660 |
| atggttatcg | cggtttgctt | tttcttcttc | ggaagccgtt | tttacagact | tcagagacct | 720 |
| ggagggagtc | cacttactag | gatctttcag | gttatagtag | cggcttttcg | gaagataagt | 780 |
| gttaaggttc | cagaggacaa | gtctctgctc | tttgaaactg | cagatgatga | gagtaacatc | 840 |
| aaaggtagcc | ggaaacttgt | gcacacagat | aacttaaagt | tttttgacaa | ggcagcggtt | 900 |
| aagagtcaat | ctgatagcat | caaagacggg | gaagtcaatc | catggagact | atgttctgtt | 960 |
| actcaagttg | aagaacttaa | gtcaataatc | acacttcttc | cagtttgggc | acaggaata | 1020 |
| gtcttcgcca | cagtgtacag | ccaaatgagc | acaatgtttg | tgttacaagg | aaacacaatg | 1080 |
| gaccaacaca | tgggaaaaaa | ctttgaaatc | ccatcagctt | cactctcact | tttcgacact | 1140 |
| gtcagtgtac | tcttctggac | tcctgtctat | gaccagttca | ttatcccgct | ggcaagaaag | 1200 |
| ttcacacgca | atgaacgagg | cttcactcag | cttcaacgta | tgggtatagg | tcttgtggtc | 1260 |
| tccatctttg | ccatgatcac | tgcaggagtc | ttggaggttg | tcaggcttga | ttatgtcaaa | 1320 |
| actcacaatg | catatgacca | aaaacagatc | catatgtcga | tattctggca | gataccgcag | 1380 |
| tatttactta | tcggttgtgc | agaagttttc | acctttatag | gtcagcttga | gttttctat | 1440 |
| gatcaggctc | ctgatgccat | gagaagtctc | tgctctgctt | tgtcgttgac | cacggttgcg | 1500 |
| ttggggaact | atttgagcac | agttcttgtg | acggttgtga | tgaagataac | gaagaagaac | 1560 |
| ggtaaaccgg | gttggatacc | ggataacttg | aaccgaggcc | atcttgatta | cttttctac | 1620 |
| ttgttggcaa | ctctcagttt | cctcaacttc | ttagtgtacc | tctggatttc | aaaacgctac | 1680 |
| aaatacaaga | agctgttggt | cgagcacat | aaatgctgca | gtctcgagcc | gatcgttcaa | 1740 |
| acatttggca | ataaagtttc | ttaa | | | | 1764 |

<210> SEQ ID NO 4
<211> LENGTH: 587
<212> TYPE: PRT
<213> ORGANISM: Arabidopsis thaliana

```
<220> FEATURE:
<221> NAME/KEY: misc_feature
<222> LOCATION: (96)..(499)
<223> OTHER INFORMATION: Pfam Name: PTR2; Pfam Description: POT family

<400> SEQUENCE: 4

Met Glu Glu Lys Asp Val Tyr Thr Gln Asp Gly Thr Val Asp Ile His
1               5                   10                  15

Asn Asn Pro Ala Asn Lys Glu Lys Thr Gly Asn Trp Lys Ala Cys Arg
            20                  25                  30

Phe Ile Leu Gly Asn Glu Cys Cys Glu Arg Leu Ala Tyr Tyr Gly Met
        35                  40                  45

Gly Thr Asn Leu Val Asn Tyr Leu Glu Ser Arg Leu Asn Gln Gly Asn
    50                  55                  60

Ala Thr Ala Ala Asn Asn Val Thr Asn Trp Ser Gly Thr Cys Tyr Ile
65                  70                  75                  80

Thr Pro Leu Ile Gly Ala Phe Ile Ala Asp Ala Tyr Leu Gly Arg Tyr
                85                  90                  95

Trp Thr Ile Ala Thr Phe Val Phe Ile Tyr Val Ser Gly Met Thr Leu
            100                 105                 110

Leu Thr Leu Ser Ala Ser Val Pro Gly Leu Lys Pro Gly Asn Cys Asn
        115                 120                 125

Ala Asp Thr Cys His Pro Asn Ser Ser Gln Thr Ala Val Phe Phe Val
    130                 135                 140

Ala Leu Tyr Met Ile Ala Leu Gly Thr Gly Gly Ile Lys Pro Cys Val
145                 150                 155                 160

Ser Ser Phe Gly Ala Asp Gln Phe Asp Glu Asn Asp Glu Asn Glu Lys
                165                 170                 175

Ile Lys Lys Ser Ser Phe Phe Asn Trp Phe Tyr Phe Ser Ile Asn Val
            180                 185                 190

Gly Ala Leu Ile Ala Ala Thr Val Leu Val Trp Ile Gln Met Asn Val
        195                 200                 205

Gly Trp Gly Trp Gly Phe Gly Val Pro Thr Val Ala Met Val Ile Ala
    210                 215                 220

Val Cys Phe Phe Phe Phe Gly Ser Arg Phe Tyr Arg Leu Gln Arg Pro
225                 230                 235                 240

Gly Gly Ser Pro Leu Thr Arg Ile Phe Gln Val Ile Val Ala Ala Phe
                245                 250                 255

Arg Lys Ile Ser Val Lys Val Pro Glu Asp Lys Ser Leu Leu Phe Glu
            260                 265                 270

Thr Ala Asp Asp Glu Ser Asn Ile Lys Gly Ser Arg Lys Leu Val His
        275                 280                 285

Thr Asp Asn Leu Lys Phe Phe Asp Lys Ala Ala Val Lys Ser Gln Ser
    290                 295                 300

Asp Ser Ile Lys Asp Gly Glu Val Asn Pro Trp Arg Leu Cys Ser Val
305                 310                 315                 320

Thr Gln Val Glu Glu Leu Lys Ser Ile Ile Thr Leu Leu Pro Val Trp
                325                 330                 335

Ala Thr Gly Ile Val Phe Ala Thr Val Tyr Ser Gln Met Ser Thr Met
            340                 345                 350

Phe Val Leu Gln Gly Asn Thr Met Asp Gln His Met Gly Lys Asn Phe
        355                 360                 365

Glu Ile Pro Ser Ala Ser Leu Ser Leu Phe Asp Thr Val Ser Val Leu
    370                 375                 380
```

-continued

```
Phe Trp Thr Pro Val Tyr Asp Gln Phe Ile Ile Pro Leu Ala Arg Lys
385                 390                 395                 400

Phe Thr Arg Asn Glu Arg Gly Phe Thr Gln Leu Gln Arg Met Gly Ile
            405                 410                 415

Gly Leu Val Val Ser Ile Phe Ala Met Ile Thr Ala Gly Val Leu Glu
        420                 425                 430

Val Val Arg Leu Asp Tyr Val Lys Thr His Asn Ala Tyr Asp Gln Lys
    435                 440                 445

Gln Ile His Met Ser Ile Phe Trp Gln Ile Pro Gln Tyr Leu Leu Ile
450                 455                 460

Gly Cys Ala Glu Val Phe Thr Phe Ile Gly Gln Leu Glu Phe Phe Tyr
465                 470                 475                 480

Asp Gln Ala Pro Asp Ala Met Arg Ser Leu Cys Ser Ala Leu Ser Leu
                485                 490                 495

Thr Thr Val Ala Leu Gly Asn Tyr Leu Ser Thr Val Leu Val Thr Val
            500                 505                 510

Val Met Lys Ile Thr Lys Lys Asn Gly Lys Pro Gly Trp Ile Pro Asp
        515                 520                 525

Asn Leu Asn Arg Gly His Leu Asp Tyr Phe Phe Tyr Leu Leu Ala Thr
    530                 535                 540

Leu Ser Phe Leu Asn Phe Leu Val Tyr Leu Trp Ile Ser Lys Arg Tyr
545                 550                 555                 560

Lys Tyr Lys Lys Ala Val Gly Arg Ala His Lys Cys Cys Ser Leu Glu
                565                 570                 575

Pro Ile Val Gln Thr Phe Gly Asn Lys Val Ser
            580                 585

<210> SEQ ID NO 5
<211> LENGTH: 580
<212> TYPE: PRT
<213> ORGANISM: Zea mays
<220> FEATURE:
<221> NAME/KEY: misc_feature
<222> LOCATION: (1)..(580)
<223> OTHER INFORMATION: Ceres CLONE ID no. 328378

<400> SEQUENCE: 5

Met Gly Glu Val Glu Asp Met Tyr Thr Gln Asp Gly Thr Val Asp Met
1               5                   10                  15

Lys Gly Asn Pro Ala Val Lys Lys Gly Thr Gly Asn Trp Arg Ala Cys
            20                  25                  30

Pro Tyr Ile Leu Ala Asn Glu Cys Cys Glu Arg Leu Ala Tyr Tyr Gly
        35                  40                  45

Met Ser Thr Asn Leu Val Asn Tyr Met Lys Thr Arg Leu Gly Gln Val
    50                  55                  60

Asn Ser Val Ala Ser Asn Asn Val Thr Asn Trp Gln Gly Thr Cys Tyr
65                  70                  75                  80

Ile Thr Pro Leu Ile Gly Ala Phe Phe Ala Asp Ala Tyr Met Gly Arg
                85                  90                  95

Phe Trp Thr Ile Ala Ile Phe Met Ile Ile Tyr Ile Phe Gly Leu Ala
            100                 105                 110

Leu Leu Thr Met Ala Ser Ser Val Lys Gly Leu Val Pro Thr Ser Cys
        115                 120                 125

Gly Asp Lys Asp Val Cys His Pro Thr Asp Ala Gln Ala Ala Val Val
    130                 135                 140

Phe Val Ala Leu Tyr Leu Ile Ala Leu Gly Thr Gly Gly Ile Lys Pro
```

```
            145                 150                 155                 160
Cys Val Ser Ser Phe Gly Ala Asp Gln Phe Asp Glu Asn Asp Glu Arg
                165                 170                 175
Glu Lys Lys Ser Lys Ser Ser Phe Phe Asn Trp Phe Tyr Phe Ser Ile
                180                 185                 190
Asn Ile Gly Ala Leu Val Ala Ser Thr Val Leu Val Tyr Val Gln Thr
                195                 200                 205
His Val Gly Trp Gly Trp Gly Phe Gly Ile Pro Ala Val Val Met Ala
                210                 215                 220
Ile Ala Val Gly Ser Phe Phe Val Gly Thr Pro Leu Tyr Arg His Gln
225                 230                 235                 240
Lys Pro Gly Gly Ser Pro Leu Thr Arg Ile Ala Gln Val Leu Val Ala
                245                 250                 255
Cys Ala Arg Lys Trp Asn Val Ala Val Pro Ala Asp Lys Ser Arg Leu
                260                 265                 270
His Glu Thr Val Asp Gly Glu Ser Gly Ile Glu Gly Ser Arg Lys Leu
                275                 280                 285
Glu His Ser Glu Gln Leu Ala Cys Leu Asp Arg Ala Ala Val Val Thr
                290                 295                 300
Ala Glu Asp Gly Ala Glu Ala Ser Pro Trp Arg Leu Cys Ser Val Thr
305                 310                 315                 320
Gln Val Glu Glu Leu Lys Ser Val Ile Arg Leu Leu Pro Ile Trp Ala
                325                 330                 335
Ser Gly Ile Val Phe Ala Ala Val Tyr Ser Gln Met Ser Thr Met Phe
                340                 345                 350
Val Leu Gln Gly Asn Thr Leu Asp Gln Ser Met Gly Pro Arg Phe Lys
                355                 360                 365
Ile Pro Ser Ala Thr Leu Ser Met Val Asp Thr Ile Ser Val Ile Val
                370                 375                 380
Trp Val Pro Val Tyr Asp Arg Ala Ile Val Pro Leu Val Arg Ser Tyr
385                 390                 395                 400
Thr Gly Arg Pro Arg Gly Phe Thr Gln Leu Gln Arg Met Gly Ile Gly
                405                 410                 415
Leu Val Val Ser Ile Phe Ser Met Val Ala Ala Gly Val Leu Asp Ile
                420                 425                 430
Val Arg Leu Arg Ala Ile Ala Arg His Gly Leu Tyr Gly Glu Asp Asp
                435                 440                 445
Ile Val Pro Ile Ser Ile Phe Trp Gln Ile Pro Gln Tyr Phe Ile Ile
                450                 455                 460
Gly Cys Ala Glu Val Phe Thr Phe Val Gly Gln Leu Glu Phe Phe Tyr
465                 470                 475                 480
Asp Gln Ala Pro Asp Ala Met Arg Ser Met Cys Ser Ala Leu Ser Leu
                485                 490                 495
Thr Thr Val Ala Leu Gly Asn Tyr Leu Ser Thr Val Leu Val Thr Ile
                500                 505                 510
Val Thr His Ile Thr Thr Arg His Gly Arg Ile Gly Trp Ile Pro Glu
                515                 520                 525
Asn Leu Asn Arg Gly His Leu Asp Tyr Phe Phe Trp Leu Leu Ala Val
                530                 535                 540
Leu Ser Leu Leu Asn Phe Leu Ala Tyr Leu Val Ile Ala Ser Trp Tyr
545                 550                 555                 560
Lys Tyr Lys Lys Thr Ala Asp Asp Tyr Pro Gly Ala Lys Gly Glu His
                565                 570                 575
```

```
Gly Thr Glu His
            580

<210> SEQ ID NO 6
<211> LENGTH: 579
<212> TYPE: PRT
<213> ORGANISM: Hordeum vulgare
<220> FEATURE:
<221> NAME/KEY: misc_feature
<222> LOCATION: (1)..(579)
<223> OTHER INFORMATION: Public GI no. 2655098

<400> SEQUENCE: 6

Met Gly Glu Val Ala Ala Glu Met Tyr Thr Gln Asp Gly Thr Val Asp
1               5                   10                  15

Ile Lys Gly Asn Pro Ala Leu Lys Lys Asp Thr Gly Asn Trp Arg Ala
                20                  25                  30

Cys Pro Tyr Ile Leu Ala Asn Glu Cys Cys Glu Arg Leu Ala Tyr Tyr
            35                  40                  45

Gly Met Ser Thr Asn Leu Val Asn Phe Met Lys Asp Arg Met Gly Met
        50                  55                  60

Ala Asn Ala Ala Ala Asn Asn Val Thr Asn Trp Gly Gly Thr Cys
65                  70                  75                  80

Tyr Ile Thr Pro Leu Ile Gly Ala Phe Leu Ala Asp Ala Tyr Leu Gly
                85                  90                  95

Arg Phe Trp Thr Ile Ala Ser Phe Met Ile Tyr Ile Phe Gly Leu
            100                 105                 110

Gly Leu Leu Thr Met Ala Thr Ser Val His Gly Leu Val Pro Ala Cys
        115                 120                 125

Ala Ser Lys Gly Val Cys Asp Pro Thr Pro Gly Gln Ser Ala Ala Val
130                 135                 140

Phe Ile Ala Leu Tyr Leu Ile Ala Leu Gly Thr Gly Gly Ile Lys Pro
145                 150                 155                 160

Cys Val Ser Ser Phe Gly Ala Asp Gln Phe Asp Glu His Asp Asp Val
                165                 170                 175

Glu Arg Lys Ser Lys Ser Phe Phe Asn Trp Phe Tyr Phe Ser Ile
            180                 185                 190

Asn Ile Gly Ala Leu Val Ala Ser Ser Val Leu Val Tyr Val Gln Thr
        195                 200                 205

His Val Gly Trp Ser Trp Gly Phe Gly Ile Pro Ala Val Val Met Ala
    210                 215                 220

Ile Ala Val Gly Ser Phe Phe Val Gly Thr Ser Leu Tyr Arg His Gln
225                 230                 235                 240

Arg Pro Gly Gly Ser Pro Leu Thr Arg Ile Ala Gln Val Leu Val Ala
                245                 250                 255

Ala Thr Arg Lys Leu Gly Val Ala Val Asp Gly Ser Ala Leu Tyr Glu
            260                 265                 270

Thr Ala Asp Lys Glu Ser Gly Ile Glu Gly Ser Arg Lys Leu Glu His
        275                 280                 285

Thr Arg Gln Phe Arg Phe Leu Asp Lys Ala Ala Val Glu Thr His Ala
    290                 295                 300

Asp Arg Thr Ala Ala Ala Pro Ser Pro Trp Arg Leu Cys Thr Val Thr
305                 310                 315                 320

Gln Val Glu Glu Leu Lys Ser Val Val Arg Leu Leu Pro Ile Trp Ala
                325                 330                 335
```

Ser Gly Ile Val Phe Ala Thr Val Tyr Gly Gln Met Ser Thr Met Phe
            340                 345                 350

Val Leu Gln Gly Asn Thr Leu Asp Ala Ser Met Gly Pro Lys Phe Lys
            355                 360                 365

Ile Pro Ser Ala Ser Leu Ser Ile Phe Asp Thr Leu Ser Val Ile Ala
            370                 375                 380

Trp Val Pro Val Tyr Asp Arg Ile Leu Val Pro Ala Val Arg Ser Val
385                 390                 395                 400

Thr Gly Arg Pro Arg Gly Phe Thr Gln Leu Gln Arg Met Gly Ile Gly
                405                 410                 415

Leu Val Val Ser Met Phe Ala Met Leu Ala Ala Gly Val Leu Glu Leu
            420                 425                 430

Val Arg Leu Arg Thr Ile Ala Gln His Gly Leu Tyr Gly Glu Lys Asp
            435                 440                 445

Val Val Pro Ile Ser Ile Phe Trp Gln Val Pro Gln Tyr Phe Ile Ile
            450                 455                 460

Gly Cys Ala Glu Val Phe Thr Phe Val Gly Gln Leu Glu Phe Phe Tyr
465                 470                 475                 480

Asp Gln Ala Pro Asp Ala Met Arg Ser Met Cys Ser Ala Leu Ser Leu
                485                 490                 495

Thr Thr Val Ala Leu Gly Asn Tyr Leu Ser Thr Leu Leu Val Thr Val
            500                 505                 510

Val Ala Lys Val Thr Thr Arg Gly Gly Lys Gln Gly Trp Ile Pro Asp
            515                 520                 525

Asn Leu Asn Val Gly His Leu Asp Tyr Phe Phe Trp Leu Leu Ala Ala
            530                 535                 540

Leu Ser Leu Val Asn Phe Ala Val Tyr Leu Leu Ile Ala Ser Trp Tyr
545                 550                 555                 560

Thr Tyr Lys Lys Thr Ala Gly Asp Ser Pro Asp Ala Lys Gly Gly Ala
                565                 570                 575

His Asp Gln

<210> SEQ ID NO 7
<211> LENGTH: 580
<212> TYPE: PRT
<213> ORGANISM: Oryza sativa (japonica cultivar-group)
<220> FEATURE:
<221> NAME/KEY: misc_feature
<222> LOCATION: (1)..(580)
<223> OTHER INFORMATION: Public GI no. 34895718

<400> SEQUENCE: 7

Met Gly Glu Val Ala Glu Asp Ile Tyr Thr Gln Asp Gly Thr Val Asp
1               5                   10                  15

Val Lys Gly Asn Pro Ala Thr Lys Lys Asn Thr Gly Asn Trp Arg Ala
            20                  25                  30

Cys Pro Tyr Ile Leu Ala Asn Glu Cys Cys Glu Arg Leu Ala Tyr Tyr
        35                  40                  45

Gly Met Ser Thr Asn Leu Val Asn Tyr Met Lys Thr Arg Leu Gly Gln
    50                  55                  60

Glu Ser Ala Ile Ala Ala Asn Asn Val Thr Asn Trp Ser Gly Thr Cys
65                  70                  75                  80

Tyr Ile Thr Pro Leu Leu Gly Ala Phe Leu Ala Asp Ala Tyr Met Gly
                85                  90                  95

Arg Phe Trp Thr Ile Ala Ser Phe Met Ile Ile Tyr Ile Leu Gly Leu
            100                 105                 110

-continued

```
Ala Leu Leu Thr Met Ala Ser Ser Val Lys Gly Leu Val Pro Ala Cys
        115                 120                 125

Asp Gly Gly Ala Cys His Pro Thr Glu Ala Gln Thr Gly Val Val Phe
    130                 135                 140

Leu Ala Leu Tyr Leu Ile Ala Leu Gly Thr Gly Ile Lys Pro Cys
145                 150                 155                 160

Val Ser Ser Phe Gly Ala Asp Gln Phe Asp Glu Asn Asp Glu Gly Glu
                165                 170                 175

Lys Arg Ser Lys Ser Ser Phe Phe Asn Trp Phe Tyr Phe Ser Ile Asn
            180                 185                 190

Ile Gly Ala Leu Val Ala Ser Ser Val Leu Val Tyr Val Gln Thr His
            195                 200                 205

Val Gly Trp Gly Trp Gly Phe Gly Ile Pro Ala Val Val Met Ala Val
    210                 215                 220

Ala Val Ala Ser Phe Phe Val Gly Thr Pro Leu Tyr Arg His Gln Arg
225                 230                 235                 240

Pro Gly Gly Ser Pro Leu Thr Arg Ile Ala Gln Val Leu Val Ala Ser
                245                 250                 255

Ala Arg Lys Trp Gly Val Glu Val Pro Ala Asp Gly Ser Arg Leu His
            260                 265                 270

Glu Thr Leu Asp Arg Glu Ser Gly Ile Glu Gly Ser Arg Lys Leu Glu
            275                 280                 285

His Thr Gly Gln Phe Ala Cys Leu Asp Arg Ala Ala Val Glu Thr Pro
    290                 295                 300

Glu Asp Arg Ser Ala Ala Asn Ala Ser Ala Trp Arg Leu Cys Thr Val
305                 310                 315                 320

Thr Gln Val Glu Glu Leu Lys Ser Val Val Arg Leu Leu Pro Ile Trp
                325                 330                 335

Ala Ser Gly Ile Val Phe Ala Thr Val Tyr Gly Gln Met Ser Thr Met
            340                 345                 350

Phe Val Leu Gln Gly Asn Thr Leu Asp Ala Ser Met Gly Pro His Phe
    355                 360                 365

Ser Ile Pro Ala Ala Ser Leu Ser Ile Phe Asp Thr Leu Ser Val Ile
370                 375                 380

Val Trp Val Pro Val Tyr Asp Arg Leu Ile Val Pro Ala Val Arg Ala
385                 390                 395                 400

Val Thr Gly Arg Pro Arg Gly Phe Thr Gln Leu Gln Arg Met Gly Ile
                405                 410                 415

Gly Leu Val Ile Ser Val Phe Ser Met Leu Ala Ala Gly Val Leu Asp
            420                 425                 430

Val Val Arg Leu Arg Ala Ile Ala Arg His Gly Leu Tyr Gly Asp Lys
    435                 440                 445

Asp Val Val Pro Ile Ser Ile Phe Trp Gln Val Pro Gln Tyr Phe Ile
    450                 455                 460

Ile Gly Ala Ala Glu Val Phe Thr Phe Val Gly Gln Leu Glu Phe Phe
465                 470                 475                 480

Tyr Asp Gln Ala Pro Asp Ala Met Arg Ser Met Cys Ser Ala Leu Ser
                485                 490                 495

Leu Thr Thr Val Ala Leu Gly Asn Tyr Leu Ser Thr Leu Leu Val Thr
            500                 505                 510

Ile Val Thr His Val Thr Thr Arg Asn Gly Ala Val Gly Trp Ile Pro
    515                 520                 525
```

```
Asp Asn Leu Asn Arg Gly His Leu Asp Tyr Phe Phe Trp Leu Leu Ala
        530                 535                 540

Val Leu Ser Leu Ile Asn Phe Gly Val Tyr Leu Val Ile Ala Ser Trp
545                 550                 555                 560

Tyr Thr Tyr Lys Lys Thr Ala Asp Ser Pro Asp Lys Ala Glu His
                565                 570                 575

Ala Gly Ala Asn
            580

<210> SEQ ID NO 8
<211> LENGTH: 572
<212> TYPE: PRT
<213> ORGANISM: Oryza sativa (japonica cultivar-group)
<220> FEATURE:
<221> NAME/KEY: misc_feature
<222> LOCATION: (1)..(572)
<223> OTHER INFORMATION: Public GI no. 50933627

<400> SEQUENCE: 8

Met Glu Ala Thr Thr Thr Asp Gly Thr Thr Asp His Ala Gly Lys Pro
1               5                   10                  15

Ala Val Arg Ser Lys Ser Gly Thr Trp Arg Ala Cys Pro Phe Ile Leu
            20                  25                  30

Gly Asn Glu Cys Cys Glu Arg Leu Ala Tyr Tyr Gly Met Ser Ala Asn
        35                  40                  45

Leu Val Asn Tyr Met Val Asp Arg Leu Arg Gln Gly Asn Ala Gly Ala
    50                  55                  60

Ala Ala Ser Val Asn Asn Trp Ser Gly Thr Cys Tyr Val Met Pro Leu
65                  70                  75                  80

Val Gly Ala Phe Leu Ala Asp Ala Tyr Leu Gly Arg Tyr Arg Thr Ile
                85                  90                  95

Ala Ala Phe Met Ala Leu Tyr Ile Val Gly Leu Ala Leu Leu Thr Met
            100                 105                 110

Ser Ala Ser Val Pro Gly Met Lys Pro Pro Asn Cys Ala Thr Ile Ser
        115                 120                 125

Ala Ser Ser Cys Gly Pro Ser Pro Gly Gln Ser Ala Ala Phe Phe Val
    130                 135                 140

Ala Leu Tyr Leu Ile Ala Leu Gly Thr Gly Gly Ile Lys Pro Cys Val
145                 150                 155                 160

Ser Ser Phe Gly Ala Asp Gln Phe Asp Asp Ala Asp Pro Arg Glu His
                165                 170                 175

Arg Ser Lys Ala Ser Phe Phe Asn Trp Phe Tyr Met Ser Ile Asn Val
            180                 185                 190

Gly Ala Leu Val Ala Ser Ser Val Leu Val Trp Val Gln Met Asn Val
        195                 200                 205

Gly Trp Gly Trp Gly Phe Gly Ile Pro Ala Val Ala Met Ala Val Ala
    210                 215                 220

Val Ala Ser Phe Leu Met Gly Ser Ser Leu Tyr Arg His Gln Lys Pro
225                 230                 235                 240

Gly Gly Ser Pro Leu Thr Arg Met Leu Gln Val Val Ala Ala Ala
                245                 250                 255

Arg Lys Ser Arg Val Ala Leu Pro Ala Asp Ala Ala Leu Leu Tyr
            260                 265                 270

Glu Gly Asp Lys Leu Ala Cys Gly Thr Arg Arg Leu Ala His Thr Glu
        275                 280                 285

Gln Phe Arg Trp Leu Asp Arg Ala Ala Val Val Thr Pro Thr Thr Asp
```

-continued

```
                290                 295                 300
Lys Asp Asp Thr Gly Ser Arg Trp Arg Leu Cys Pro Val Thr Gln
305                 310                 315                 320

Val Glu Glu Leu Lys Ala Val Arg Leu Leu Pro Val Trp Ala Ser
                325                 330                 335

Gly Ile Val Met Ser Ala Val Tyr Gly Gln Met Ser Thr Met Phe Val
                340                 345                 350

Leu Gln Gly Asn Thr Leu Asp Pro Arg Met Gly Ala Thr Phe Lys Ile
                355                 360                 365

Pro Ser Ala Ser Leu Ser Ile Phe Asp Thr Leu Ala Val Leu Ala Trp
370                 375                 380

Val Pro Val Tyr Asp Arg Leu Ile Val Pro Ala Ala Arg Arg Phe Thr
385                 390                 395                 400

Gly His Pro Arg Gly Phe Thr Gln Leu Gln Arg Met Gly Ile Gly Leu
                405                 410                 415

Leu Ile Ser Val Phe Ser Met Val Ala Ala Gly Val Leu Glu Val Val
                420                 425                 430

Arg Leu Arg Val Ala Ala Ala His Gly Met Leu Asp Ser Thr Ser Tyr
            435                 440                 445

Leu Pro Ile Ser Ile Phe Trp Gln Val Gln Tyr Phe Ile Ile Gly Ala
            450                 455                 460

Ala Glu Val Phe Ala Phe Ile Gly Gln Ile Asp Phe Phe Tyr Asp Gln
465                 470                 475                 480

Ala Pro Asp Asp Met Arg Ser Thr Cys Thr Ala Leu Ser Leu Thr Ser
                485                 490                 495

Ser Ala Leu Gly Asn Tyr Leu Ser Thr Leu Leu Val Val Ile Val Thr
                500                 505                 510

Ala Ala Ser Thr Arg Gly Gly Gly Leu Gly Trp Ile Pro Asp Asn Leu
                515                 520                 525

Asn Arg Gly His Leu Asp Tyr Phe Phe Trp Leu Leu Ala Ala Leu Ser
                530                 535                 540

Ala Val Asn Phe Leu Val Tyr Leu Trp Ile Ala Asn Trp Tyr Arg Cys
545                 550                 555                 560

Lys Thr Ile Thr Thr Thr Glu Ala Ala Ala Gln Thr
                565                 570

<210> SEQ ID NO 9
<211> LENGTH: 580
<212> TYPE: PRT
<213> ORGANISM: Lycopersicon esculentum
<220> FEATURE:
<221> NAME/KEY: misc_feature
<222> LOCATION: (1)..(580)
<223> OTHER INFORMATION: Public GI no. 4102839

<400> SEQUENCE: 9

Met Lys Tyr Leu Phe Ser Lys Asn Gly Gly Leu Leu Glu Asp Glu Asn
1               5                   10                  15

Ser Gly Leu Tyr Thr Arg Asp Gly Ser Val Asp Ile Lys Gly Asn Pro
                20                  25                  30

Val Leu Lys Ser Glu Thr Gly Asn Trp Arg Ala Cys Pro Phe Ile Leu
                35                  40                  45

Gly Asn Glu Cys Cys Glu Arg Leu Ala Tyr Tyr Gly Ile Ala Ala Asn
            50                  55                  60

Leu Val Thr Tyr Leu Thr Lys Lys Leu His Glu Gly Asn Val Ser Ala
65                  70                  75                  80
```

-continued

```
Ala Arg Asn Val Thr Thr Trp Gln Gly Thr Cys Tyr Ile Thr Pro Leu
                85                  90                  95
Ile Gly Ala Val Leu Ala Asp Ala Tyr Trp Arg Tyr Trp Thr Ile
            100                 105                 110
Ala Thr Phe Ser Thr Ile Tyr Phe Ile Gly Met Cys Thr Leu Thr Leu
            115                 120                 125
Ser Ala Ser Val Pro Ala Phe Lys Pro Pro Gln Cys Val Gly Ser Val
        130                 135                 140
Cys Pro Ser Ala Ser Pro Ala Gln Tyr Ala Ile Phe Phe Gly Leu
145                 150                 155                 160
Tyr Leu Ile Ala Leu Gly Thr Gly Ile Lys Pro Cys Val Ser Ser
                165                 170                 175
Phe Gly Ala Asp Gln Phe Asp Asp Thr Asp Pro Lys Glu Arg Val Lys
            180                 185                 190
Lys Gly Ser Phe Phe Asn Trp Phe Tyr Phe Ser Ile Asn Ile Gly Ala
        195                 200                 205
Leu Ile Ser Ser Ser Leu Ile Val Trp Ile Gln Glu Asn Ala Gly Trp
    210                 215                 220
Gly Leu Gly Phe Gly Ile Pro Ala Val Phe Met Gly Ile Ala Ile Ala
225                 230                 235                 240
Ser Phe Phe Phe Gly Thr Pro Leu Tyr Arg Phe Gln Lys Pro Gly Gly
                245                 250                 255
Ser Pro Leu Thr Arg Met Cys Gln Val Leu Val Ala Val Phe His Lys
            260                 265                 270
Trp Asn Leu Ser Val Pro Asp Asp Ser Thr Leu Leu Tyr Glu Thr Pro
        275                 280                 285
Asp Lys Ser Ser Ala Ile Glu Gly Ser Arg Lys Leu Leu His Thr Asp
    290                 295                 300
Glu Leu Arg Cys Leu Asp Lys Ala Ala Val Val Ser Asp Asn Glu Leu
305                 310                 315                 320
Thr Thr Gly Asp Tyr Ser Asn Ala Trp Arg Leu Cys Thr Val Thr Gln
                325                 330                 335
Val Glu Glu Leu Lys Ile Leu Ile Arg Met Phe Pro Ile Trp Ala Thr
            340                 345                 350
Gly Ile Val Phe Ser Ala Val Tyr Ala Gln Met Ser Thr Met Phe Val
        355                 360                 365
Glu Gln Gly Met Val Met Asp Thr Ala Val Gly Ser Phe Lys Ile Pro
    370                 375                 380
Ala Ala Ser Leu Ser Thr Phe Asp Thr Ile Ser Val Ile Val Trp Val
385                 390                 395                 400
Pro Val Tyr Asp Lys Ile Leu Val Pro Ile Ala Arg Arg Phe Thr Gly
                405                 410                 415
Ile Glu Arg Gly Phe Ser Glu Leu Gln Arg Met Gly Ile Gly Leu Phe
            420                 425                 430
Leu Ser Met Leu Cys Met Ser Ala Ala Ile Val Glu Ile Arg Arg
        435                 440                 445
Leu Gln Leu Ala Arg Asp Leu Gly Leu Val Asp Glu Ala Val Ser Val
    450                 455                 460
Pro Leu Ser Ile Phe Trp Gln Ile Pro Gln Tyr Phe Ile Leu Gly Ala
465                 470                 475                 480
Ala Glu Ile Phe Thr Phe Ile Gly Gln Leu Glu Phe Phe Tyr Asp Gln
                485                 490                 495
```

-continued

```
Ser Pro Asp Ala Met Arg Ser Leu Cys Ser Ala Leu Ser Leu Leu Thr
            500                 505                 510

Thr Ala Leu Gly Asn Tyr Leu Ser Ser Phe Ile Leu Thr Val Val Thr
            515                 520                 525

Ser Ile Thr Thr Arg Gly Gly Lys Pro Gly Trp Ile Pro Asn Asn Leu
            530                 535                 540

Asn Gly Gly His Leu Asp Tyr Phe Phe Trp Leu Leu Ala Ala Leu Ser
545                 550                 555                 560

Phe Phe Asn Leu Val Ile Tyr Val Phe Leu Cys Gln Met Tyr Lys Ser
                565                 570                 575

Lys Lys Ala Ser
            580

<210> SEQ ID NO 10
<211> LENGTH: 584
<212> TYPE: PRT
<213> ORGANISM: Vicia faba
<220> FEATURE:
<221> NAME/KEY: misc_feature
<222> LOCATION: (1)..(584)
<223> OTHER INFORMATION: Public GI no. 31088360

<400> SEQUENCE: 10

Met Gly Ser Val Glu Asp Ser Ser Arg Leu Glu Glu Ala Leu Ile
1               5                   10                  15

Gln Asp Glu Glu Ser Lys Leu Tyr Thr Gly Asp Gly Ser Val Asp Phe
            20                  25                  30

Lys Gly Arg Pro Val Leu Lys Lys Asn Thr Gly Asn Trp Lys Ala Cys
        35                  40                  45

Pro Phe Ile Leu Gly Asn Glu Cys Cys Glu Arg Leu Ala Tyr Tyr Gly
    50                  55                  60

Ile Ala Thr Asn Leu Val Lys Pro Ile Leu Ala Lys Leu His Glu
65                  70                  75                  80

Gly Asn Val Ser Ala Ala Arg Asn Val Thr Thr Trp Gln Gly Thr Cys
                85                  90                  95

Tyr Leu Ala Pro Leu Ile Gly Ala Val Leu Ala Asp Ser Tyr Trp Gly
            100                 105                 110

Arg Tyr Trp Thr Ile Ala Ile Phe Ser Met Ile Tyr Phe Ile Gly Met
        115                 120                 125

Gly Thr Leu Thr Leu Ser Ala Ser Ile Pro Ala Leu Lys Pro Ala Glu
    130                 135                 140

Cys Leu Gly Ala Val Cys Pro Pro Ala Thr Pro Ala Gln Tyr Ala Val
145                 150                 155                 160

Phe Phe Ile Gly Leu Tyr Leu Ile Ala Leu Gly Thr Gly Ile Lys
                165                 170                 175

Pro Cys Val Ser Ser Phe Gly Ala Asp Gln Phe Asp Asp Thr Asp Ser
            180                 185                 190

Arg Glu Arg Val Lys Lys Gly Ser Phe Phe Asn Trp Phe Tyr Phe Ser
        195                 200                 205

Ile Asn Ile Gly Ala Leu Ile Ser Ser Ser Phe Ile Val Trp Ile Gln
    210                 215                 220

Glu Asn Ala Gly Trp Gly Leu Gly Phe Gly Ile Pro Ala Leu Phe Met
225                 230                 235                 240

Gly Leu Ala Ile Gly Ser Phe Phe Leu Gly Thr Pro Leu Tyr Arg Phe
                245                 250                 255

Gln Lys Pro Gly Gly Ser Pro Leu Thr Arg Met Cys Gln Val Val Ala
```

-continued

```
                260                 265                 270
Ala Ser Phe Arg Lys Arg Asn Leu Thr Val Pro Glu Asp Ser Ser Leu
            275                 280                 285

Leu Tyr Glu Thr Pro Asp Lys Ser Ser Ala Ile Glu Gly Ser Arg Lys
        290                 295                 300

Leu Gln His Ser Asp Glu Leu Arg Cys Leu Asp Arg Ala Ala Val Ile
305                 310                 315                 320

Ser Asp Asp Glu Arg Lys Arg Gly Asp Tyr Ser Asn Leu Trp Arg Leu
                325                 330                 335

Cys Thr Val Thr Gln Val Glu Glu Leu Lys Ile Leu Ile Arg Met Phe
            340                 345                 350

Pro Val Trp Ala Thr Gly Ile Val Phe Ser Ala Val Tyr Ala Gln Met
        355                 360                 365

Ser Thr Met Phe Val Glu Gln Gly Thr Met Met Asp Thr Ser Val Gly
    370                 375                 380

Ser Phe Lys Ile Pro Ala Ala Ser Leu Ser Thr Phe Asp Val Ile Ser
385                 390                 395                 400

Val Ile Phe Trp Val Pro Val Tyr Asp Arg Phe Ile Val Pro Ile Ala
                405                 410                 415

Arg Lys Phe Thr Gly Lys Glu Arg Gly Phe Ser Glu Leu Gln Arg Met
            420                 425                 430

Gly Ile Gly Leu Phe Ile Ser Val Leu Cys Met Ser Ala Ala Ala Ile
        435                 440                 445

Val Glu Ile Lys Arg Leu Gln Leu Ala Lys Glu Leu Asp Leu Val Asp
    450                 455                 460

Lys Ala Val Pro Val Pro Leu Thr Ile Phe Leu Gln Ile Pro Gln Tyr
465                 470                 475                 480

Phe Leu Leu Gly Ala Ala Glu Val Phe Thr Phe Val Gly Gln Leu Glu
                485                 490                 495

Phe Phe Tyr Asp Gln Ser Pro Asp Ala Met Arg Ser Leu Cys Ser Ala
            500                 505                 510

Leu Ser Leu Leu Thr Thr Ser Leu Gly Asn Tyr Leu Ser Ser Phe Ile
        515                 520                 525

Leu Thr Val Val Leu Tyr Phe Thr Thr Arg Gly Gly Asn Pro Gly Trp
    530                 535                 540

Ile Pro Asp Asn Leu Asn Lys Gly His Leu Asp Tyr Phe Ser Gly Leu
545                 550                 555                 560

Ala Gly Leu Ser Phe Leu Asn Met Phe Leu Tyr Ile Val Ala Ala Lys
                565                 570                 575

Arg Tyr Lys Ser Lys Lys Ala Ser
            580
```

<210> SEQ ID NO 11
<211> LENGTH: 559
<212> TYPE: PRT
<213> ORGANISM: Prunus dulcis
<220> FEATURE:
<221> NAME/KEY: misc_feature
<222> LOCATION: (1)..(559)
<223> OTHER INFORMATION: Public GI no. 6635838
<220> FEATURE:
<221> NAME/KEY: misc_feature
<222> LOCATION: (46)..(46)
<223> OTHER INFORMATION: Xaa is any aa, unknown, or other

<400> SEQUENCE: 11

Met Gly Ser Leu Glu Glu Glu Arg Ser Leu Leu Glu Asp Gly Leu Ile

```
1               5                   10                  15
Gln Asp Glu Thr Asn Gly Leu Tyr Thr Gly Asp Gly Ser Val Asp Ile
                20                  25                  30

Thr Gly Lys Pro Val Leu Lys Gln Ser Thr Gly Asn Trp Xaa Ala Cys
            35                  40                  45

Pro Phe Ile Leu Gly Thr Glu Cys Cys Glu Arg Leu Ala Phe Tyr Gly
        50                  55                  60

Ile Ser Thr Asn Leu Val Thr Tyr Leu Thr His Lys Leu His Glu Gly
65                  70                  75                  80

Asn Val Ser Ala Ala Arg Asn Val Thr Thr Trp Ser Gly Thr Cys Tyr
                85                  90                  95

Leu Thr Pro Leu Ile Gly Ala Val Leu Ala Asp Ala Tyr Trp Gly Arg
            100                 105                 110

Tyr Trp Thr Ile Ala Ile Phe Ser Thr Ile Tyr Phe Ile Gly Met Cys
        115                 120                 125

Thr Leu Thr Ile Ser Ala Ser Val Pro Ala Leu Lys Pro Pro Gln Cys
            130                 135                 140

Val Asp Ser Val Cys Pro Ser Ala Ser Pro Ala Gln Tyr Gly Val Phe
145                 150                 155                 160

Phe Phe Gly Leu Tyr Leu Ile Ala Leu Arg Thr Gly Gly Ile Lys Pro
                165                 170                 175

Cys Val Ser Ser Phe Gly Ala Asp Gln Phe Asp Asp Thr Asp Ser Arg
            180                 185                 190

Glu Arg Val Lys Lys Gly Ser Phe Phe Asn Trp Phe Tyr Phe Ser Ile
        195                 200                 205

Asn Ile Gly Ala Leu Val Ser Ser Thr Leu Ile Val Trp Val Gln Asp
210                 215                 220

Asn Ala Gly Trp Gly Leu Gly Phe Gly Ile Pro Ala Leu Phe Met Gly
225                 230                 235                 240

Ile Ala Ile Val Ser Phe Phe Ser Gly Thr Pro Leu Tyr Arg Phe Gln
                245                 250                 255

Lys Pro Gly Gly Ser Pro Leu Thr Arg Met Cys Gln Val Leu Val Ala
            260                 265                 270

Ser Phe Arg Lys Trp Asn Leu Asp Val Pro Arg Asp Ser Ser Leu Leu
        275                 280                 285

Tyr Glu Thr Gln Asp Lys Gly Ser Ala Ile Lys Gly Ser Arg Lys Leu
            290                 295                 300

Glu His Ser Asp Glu Leu Asn Cys Leu Asp Lys Ala Ala Val Ile Ser
305                 310                 315                 320

Glu Thr Glu Thr Lys Thr Gly Asp Phe Ser Asn Pro Trp Arg Ile Cys
                325                 330                 335

Thr Val Thr Gln Val Glu Glu Leu Lys Ile Leu Ile Arg Met Phe Pro
            340                 345                 350

Ile Trp Ala Thr Gly Ile Val Phe Ser Ala Val Tyr Ala Gln Met Ala
        355                 360                 365

Thr Met Phe Val Glu Gln Gly Met Met Met Asp Thr Ser Val Gly Ser
            370                 375                 380

Phe Thr Ile Pro Pro Ala Ser Leu Ser Ser Phe Asp Val Ile Ser Val
385                 390                 395                 400

Ile Phe Trp Val Pro Ile Tyr Asp Arg Phe Ile Val Pro Ile Ala Arg
                405                 410                 415

Lys Phe Thr Gly Lys Glu Arg Gly Phe Ser Glu Leu Gln Arg Met Gly
            420                 425                 430
```

```
Ile Gly Leu Phe Leu Ser Val Leu Cys Met Ser Ala Ala Ala Val Val
            435                 440                 445

Glu Met Lys Arg Leu Gln Leu Ala Thr Glu Leu Gly Leu Val Asp Lys
450                 455                 460

Glu Val Ala Val Pro Leu Ser Ile Phe Trp Gln Ile Pro Gln Tyr Phe
465                 470                 475                 480

Leu Leu Gly Ala Ala Glu Ile Phe Thr Phe Ile Gly Gln Leu Glu Phe
                485                 490                 495

Phe Tyr Asp Gln Ser Ser Asp Ala Met Arg Ser Leu Cys Ser Ala Leu
            500                 505                 510

Ser Ala Ser Asp Asp Phe Ile Gly Lys Leu Ser Glu Leu Phe Asp Ser
            515                 520                 525

Asp Ile Val Thr Tyr Phe Thr Thr Gln Gly Gly Lys Ala Gly Trp Ile
            530                 535                 540

Pro Asp Asn Leu Asn Asp Gly His Leu Asp Tyr Phe Ser Gly Ser
545                 550                 555
```

<210> SEQ ID NO 12
<211> LENGTH: 557
<212> TYPE: PRT
<213> ORGANISM: Oryza sativa (japonica cultivar-group)
<220> FEATURE:
<221> NAME/KEY: misc_feature
<222> LOCATION: (1)..(557)
<223> OTHER INFORMATION: Public GI no. 56784523

<400> SEQUENCE: 12

```
Met Glu Gly Val Glu Ser Cys Asn Gly Arg His Ala Asp Ala Asp Asp
1               5                   10                  15

Arg Arg Thr Ser Lys Lys Asp Arg Arg Thr Thr Trp Ala Ser Ala Phe
            20                  25                  30

Ile Leu Val Asn Asn Phe Met Gln Tyr Thr Ala Tyr Phe Gly Val Ser
        35                  40                  45

Thr Asn Leu Val Asn Tyr Leu Lys Tyr Arg Leu His Glu Gly Ser Lys
    50                  55                  60

Ser Ala Ala Asn Asp Val Thr Asn Trp Gln Gly Thr Gly Ser Ile Thr
65                  70                  75                  80

Pro Leu Val Ala Ala Tyr Leu Ala Asp Ala Phe Leu Gly Arg Tyr Trp
                85                  90                  95

Thr Ile Leu Leu Phe Met Ala Ile Ser Val Leu Gly Tyr Gly Val Leu
            100                 105                 110

Ala Ala Ser Ala Ala Ala Pro Ala Leu Leu His Gly Ala Ala Ala
            115                 120                 125

Phe Tyr Ala Gly Leu Tyr Leu Val Ala Leu Gly Ser Gly Leu Leu Val
    130                 135                 140

Val Met Ala Pro Phe Gly Ala Gly Gln Phe Asp Glu Ala Asp Glu Gly
145                 150                 155                 160

Glu Arg Arg Arg Gln Ser Ser Phe Phe Asn Trp Phe Tyr Leu Ser Leu
                165                 170                 175

Asn Phe Gly Ser Leu Val Gly Gly Thr Val Leu Val Trp Val Gln Thr
            180                 185                 190

Ser Val Gly Trp Gly Ile Gly Tyr Gly Val Pro Ala Ile Phe Ser Ala
        195                 200                 205

Leu Ser Val Ala Val Phe Leu Ala Gly Thr Ala Ala Tyr Arg Arg Cys
    210                 215                 220
```

Gln Pro Pro Gly Gly Ser Pro Leu Thr Arg Ile Ala Gln Val Val
225                 230                 235                 240

Ala Ala Ala Arg Lys His Asp Val Glu Val Pro Ala Asp Ala Ser Leu
            245                 250                 255

Leu His Glu Cys Cys Asp Ala Val Asp Gly Met Ser Ala Ile Gln Gly
        260                 265                 270

Ser Arg Arg Leu Val His Thr Asp Gln Phe Arg Phe Leu Asp Lys Ala
    275                 280                 285

Ala Val Glu Thr Ala Gly Asp Lys Ala Glu Pro Ser Pro Trp Arg Leu
290                 295                 300

Cys Thr Val Thr Gln Val Glu Leu Lys Cys Val Leu Arg Leu Leu
305                 310                 315                 320

Pro Val Trp Ala Ser Gly Ile Ile Phe Ala Ala Tyr Thr Gln Met
                325                 330                 335

Thr Thr Thr Phe Val Leu Gln Gly Asp Thr Leu Asp Pro Arg Ile Gly
            340                 345                 350

Gly Phe Lys Val Pro Ala Ala Val Leu Ser Val Phe Asp Thr Leu Ser
        355                 360                 365

Val Met Leu Trp Val Pro Leu Tyr Asp Arg Ala Ile Val Pro Leu Ala
    370                 375                 380

Arg Arg Val Thr Gly His Asp Arg Gly Phe Thr Gln Leu Ala Arg Met
385                 390                 395                 400

Gly Val Gly Leu Val Ile Leu Thr Val Ala Met Leu Val Ala Gly Thr
                405                 410                 415

Leu Glu Val Ala Arg Arg Val Ile Ala Arg His Gly Leu Tyr Gly
            420                 425                 430

Asp Asp Gly Asp Gly Gly Tyr Leu Pro Leu Ser Ile Phe Trp Gln Val
        435                 440                 445

Pro Gln Tyr Val Val Val Gly Ala Ser Glu Val Phe Thr Phe Ile Gly
    450                 455                 460

Gln Met Glu Phe Phe Tyr Asp Gln Ala Pro Asp Ala Met Arg Ser Leu
465                 470                 475                 480

Cys Ser Gly Leu Ser Ser Thr Ser Phe Ala Leu Gly Asn Tyr Ala Ser
                485                 490                 495

Ser Ala Ile Val Val Val Ala Arg Ala Thr Ala Arg Gly Gly Arg
            500                 505                 510

Leu Gly Trp Ile Pro Asp Asn Ile Asn Arg Gly His Leu Asp Asp Phe
        515                 520                 525

Phe Trp Leu Leu Ala Val Leu Cys Val Ala Asn Phe Ala Ala Tyr Leu
    530                 535                 540

Leu Ile Ala Arg Trp Tyr Thr Tyr Lys Lys Thr Val Asp
545                 550                 555

<210> SEQ ID NO 13
<211> LENGTH: 545
<212> TYPE: PRT
<213> ORGANISM: Oryza sativa (japonica cultivar-group)
<220> FEATURE:
<221> NAME/KEY: misc_feature
<222> LOCATION: (1)..(545)
<223> OTHER INFORMATION: Public GI no. 56784524

<400> SEQUENCE: 13

Met Glu Gly Val Glu Ser Asn Asp Arg His Gly Gly Ala Ala Ala Asp
1               5                   10                  15

Arg Arg Lys Ser Asn Arg Arg Asn Arg Trp Ala Cys Thr Phe Ile Leu

-continued

```
                20                  25                  30
Ala Asn Asn Phe Phe Gln Asn Met Ala Tyr Phe Gly Val Ser Thr Asn
                35                  40                  45
Leu Val Asn Tyr Leu Lys Tyr Arg Leu His Glu Gly Ser Lys Ser Ala
         50                  55                  60
Ala Asn Asn Val Thr Asn Trp Glu Gly Thr Gly Ser Ile Ala Pro Leu
 65                  70                  75                  80
Val Ala Gly Tyr Leu Ala Asp Ala Phe Leu Gly Arg Tyr Trp Thr Ile
                 85                  90                  95
Val Leu Ser Met Val Ile Ser Ala Val Arg Ser Ser Pro Pro Pro
                100                 105                 110
Ala Met Gln Gly Tyr Gly Val Leu Ala Ala Ser Ala Ser Val Ile Arg
                115                 120                 125
Leu Glu Ser Ala Ala Leu Tyr Ala Gly Met Tyr Leu Val Ala Leu Gly
            130                 135                 140
Gly Val Leu Glu Pro Ile Met Ala Pro Phe Gly Ala Asp Gln Phe Asp
145                 150                 155                 160
Asp Gly Glu Asp Asp Gln Arg Gly Arg Arg Gln Ser Ser Phe Phe Asn
                    165                 170                 175
Trp Phe Tyr Leu Ser Leu Asn Cys Gly Ser Leu Val Gly Gly Thr Val
            180                 185                 190
Leu Val Trp Val Gln Thr Ser Val Gly Trp Gly Val Gly Tyr Gly Val
            195                 200                 205
Pro Ala Ile Phe Ser Ala Leu Ser Val Ala Val Phe Leu Ala Gly Thr
210                 215                 220
Ala Thr Tyr Arg Arg Asp Gln Pro Pro Gly Gly Ser Pro Leu Thr Arg
225                 230                 235                 240
Ile Ala Gln Val Val Ala Ala Val Arg Lys Phe Asp Val Glu Ile
                245                 250                 255
Pro Ser Asp Ser Ser Met Leu Tyr Glu Ser Asp Ala Val Asp Gly Met
                260                 265                 270
Pro Ala Ile His Gly Arg Arg Leu Leu His Thr Gly Gln Phe Arg
                275                 280                 285
Phe Leu Asp Arg Ala Thr Val Lys Thr Ala Gly Glu Lys Ala Ala Gln
        290                 295                 300
Ser Pro Trp Arg Leu Cys Thr Val Thr Gln Val Glu Glu Leu Lys Cys
305                 310                 315                 320
Val Leu Arg Leu Leu Pro Val Trp Ala Thr Gly Ile Ile Tyr Ala Ala
                    325                 330                 335
Ala Tyr Thr Gln Val Thr Thr Thr Phe Ile Leu Gln Gly Asp Thr Leu
                340                 345                 350
Asp Arg Ser Leu Gly Arg Phe Lys Val Pro Ala Ala Ala Leu Ser Ile
            355                 360                 365
Phe His Thr Leu Ser Val Ile Leu Trp Val Ala Leu Tyr Asp Arg Ala
            370                 375                 380
Ile Val Pro Leu Ala Arg Arg Val Thr Arg His Asp Gly Gly Phe Thr
385                 390                 395                 400
Gln Leu Ala Arg Met Gly Val Gly Leu Val Ile Leu Thr Val Ala Met
                405                 410                 415
Ala Ala Ala Gly Ala Leu Glu Ala Ala Arg Arg Arg Leu Ile Ala Arg
                420                 425                 430
Pro Ser Val Phe Trp Gln Val Pro Gln Tyr Ala Val Val Gly Ala Ser
            435                 440                 445
```

```
Glu Val Phe Thr Leu Ile Gly Gln Met Glu Phe Phe Tyr Asp Gln Ala
            450                 455                 460

Pro Asp Ala Met Arg Ser Leu Cys Ser Ala Leu Ser Ser Thr Ser Phe
465                 470                 475                 480

Ala Leu Gly Asp Tyr Ala Ser Ser Ala Leu Val Val Ala Ala Arg
                485                 490                 495

Arg Gly Gly Ala Pro Gly Trp Ile Pro Asp Asp Ile Asn Arg Gly His
                500                 505                 510

Leu Asp Tyr Phe Phe Trp Leu Leu Thr Ala Leu Cys Val Ala Asn Phe
            515                 520                 525

Ala Ala Tyr Leu Leu Ile Ala Arg Trp Tyr Thr Tyr Lys Lys Thr Val
530                 535                 540

Asp
545

<210> SEQ ID NO 14
<211> LENGTH: 586
<212> TYPE: PRT
<213> ORGANISM: Triticum aestivum
<220> FEATURE:
<221> NAME/KEY: misc_feature
<222> LOCATION: (1)..(586)
<223> OTHER INFORMATION: Public GI no. 50059161

<400> SEQUENCE: 14

Met Asp Ser Thr Asp Gln Phe Asp Asn Ser Pro Leu Leu Asp Gly Asp
1               5                   10                  15

Gly Ser Ser Gln Glu Asn Thr Thr Glu Tyr Thr Gly Asp Gly Ser Val
            20                  25                  30

Cys Ile Ser Gly His Pro Ala Ser Arg Lys His Thr Gly Asn Trp Lys
        35                  40                  45

Ala Ser Phe Leu Ile Ile Val Cys Ser Phe Cys Cys Tyr Leu Ala Tyr
    50                  55                  60

Ser Ser Ile Gly Lys Asn Leu Val Ser Tyr Leu Thr Lys Val Leu His
65                  70                  75                  80

Glu Thr Asn Leu Asp Ala Ala Arg His Val Ala Thr Trp Gln Gly Thr
                85                  90                  95

Ser Tyr Leu Ala Pro Leu Val Gly Ala Phe Val Ala Asp Ser Tyr Leu
            100                 105                 110

Gly Lys Tyr Arg Thr Ala Leu Ile Ala Cys Lys Ile Phe Ile Ile Gly
        115                 120                 125

Met Met Met Leu Leu Leu Ser Ala Ala Leu Gln Leu Ile Ser Ala Gly
    130                 135                 140

Pro His Ala Trp Thr Val Trp Val His Leu Val Ser Ser Gln Tyr Thr
145                 150                 155                 160

Ile Phe Leu Ile Gly Leu Tyr Met Val Gly Leu Gly Tyr Gly Ala Gln
                165                 170                 175

Arg Pro Cys Val Thr Ser Phe Gly Ala Asp Gln Phe Asp Asp Thr Asp
            180                 185                 190

Tyr Val Glu Lys Thr Arg Lys Ser Ser Phe Phe Asn Trp His Tyr Phe
        195                 200                 205

Ala Ile Asn Ala Gly Ser Leu Ile Ala Gly Thr Val Ile Val Trp Val
    210                 215                 220

Gln Glu His Glu Gly Trp Leu Trp Gly Phe Thr Ile Ser Thr Leu Phe
225                 230                 235                 240
```

```
Val Thr Leu Gly Val Cys Ile Phe Phe Leu Gly Ser Ile Val Tyr Arg
                245                 250                 255

Phe Gln Lys Pro Arg Gly Ser Pro Leu Thr Arg Leu Cys Gln Val Val
            260                 265                 270

Ile Ala Ala Thr Arg Asn Phe Asp Lys Val Leu Pro Cys Asp Ser Ser
        275                 280                 285

Ala Leu Tyr Glu Phe Met Gly Gln Gly Ser Ala Ile Glu Gly Arg Arg
    290                 295                 300

Lys Leu Glu His Thr Thr Gly Leu Gly Phe Phe Asp Lys Ala Ala Ile
305                 310                 315                 320

Val Thr Leu Pro Asp Cys Glu Ser Pro Gly Gln His Asn Lys Trp Lys
                325                 330                 335

Ile Cys Thr Val Thr Gln Val Glu Glu Leu Lys Ile Leu Ile Arg Met
            340                 345                 350

Phe Pro Ile Trp Ser Ala Met Ile Leu Phe Ala Ala Val Gln Glu Gln
        355                 360                 365

Met Ser Ser Thr Phe Val Glu Gln Gly Met Ala Met Asp Lys His Ile
    370                 375                 380

Gly Ser Phe Glu Ile Pro Ser Ala Ser Phe Gln Cys Val Asp Thr Ile
385                 390                 395                 400

Thr Val Ile Val Leu Val Pro Ile Tyr Glu Arg Leu Ile Val Pro Val
                405                 410                 415

Ile Arg Lys Phe Thr Gly Arg Ala Asn Gly Ile Thr Ser Pro Gln Arg
            420                 425                 430

Ile Gly Ile Gly Leu Cys Phe Ser Met Phe Ser Met Val Ser Ala Ala
        435                 440                 445

Leu Val Glu Gly Asn Arg Leu Gln Ile Ala Gln Ala Glu Gly Leu Val
    450                 455                 460

His Arg Lys Val Ala Val Pro Met Ser Ile Met Trp Gln Gly Pro Gln
465                 470                 475                 480

Tyr Phe Leu Leu Gly Val Ala Glu Val Phe Ser Asn Ile Gly Leu Thr
                485                 490                 495

Glu Ala Phe Tyr Asp Glu Ser Pro Asp Gly Met Arg Ser Leu Cys Met
            500                 505                 510

Ala Phe Ser Leu Val Asn Met Ser Ala Gly Asn Tyr Leu Ser Ser Leu
        515                 520                 525

Ile Leu Ser Leu Val Pro Val Phe Thr Ala Arg Gly Gly Ser Pro Gly
    530                 535                 540

Trp Ile Pro Asp Asn Leu Asn Glu Gly His Leu Asp Arg Phe Tyr Leu
545                 550                 555                 560

Met Met Ala Gly Leu Ser Phe Phe Asn Ile Val Val Phe Val Phe Cys
                565                 570                 575

Ala Met Arg Tyr Lys Cys Lys Lys Ala Ser
            580                 585

<210> SEQ ID NO 15
<211> LENGTH: 584
<212> TYPE: PRT
<213> ORGANISM: Oryza sativa
<220> FEATURE:
<221> NAME/KEY: misc_feature
<222> LOCATION: (1)..(584)
<223> OTHER INFORMATION: Public GI no. 6409176

<400> SEQUENCE: 15

Met Asp Ser Ser Tyr Gln His Asp Lys Pro Leu Leu Asp Glu Glu Asn
```

```
1               5                   10                  15
Ser Ser Gln Val Thr Leu Glu Tyr Thr Gly Asp Gly Ser Val Cys Ile
                20                  25                  30

Arg Gly His Pro Ala Leu Arg Lys His Thr Gly Asn Trp Lys Gly Ser
                35                  40                  45

Ser Leu Ala Ile Val Phe Ser Phe Cys Ser Tyr Leu Ala Phe Thr Ser
                50                  55                  60

Ile Val Lys Asn Leu Val Ser Tyr Leu Thr Lys Val Leu His Glu Thr
65                  70                  75                  80

Asn Val Ala Ala Ala Arg Asp Val Ala Thr Trp Ser Gly Thr Ser Tyr
                85                  90                  95

Leu Ala Pro Leu Val Gly Ala Phe Leu Ala Asp Ser Tyr Leu Gly Lys
                100                 105                 110

Tyr Cys Thr Ile Leu Ile Phe Cys Thr Ile Phe Ile Ile Gly Leu Met
                115                 120                 125

Met Leu Leu Leu Ser Ala Ala Val Pro Leu Ile Ser Thr Gly Pro His
                130                 135                 140

Ser Trp Ile Ile Trp Thr Asp Pro Val Ser Ser Gln Asn Ile Ile Phe
145                 150                 155                 160

Phe Val Gly Leu Tyr Met Val Ala Leu Gly Tyr Gly Ala Gln Cys Pro
                165                 170                 175

Cys Ile Ser Ser Phe Gly Ala Asp Gln Phe Asp Asp Thr Asp Glu Asn
                180                 185                 190

Glu Arg Thr Lys Lys Ser Ser Phe Phe Asn Trp Thr Tyr Phe Val Ala
                195                 200                 205

Asn Ala Gly Ser Leu Ile Ser Gly Thr Val Ile Val Trp Val Gln Asp
                210                 215                 220

His Lys Gly Trp Ile Trp Gly Phe Thr Ile Ser Ala Leu Phe Val Tyr
225                 230                 235                 240

Leu Gly Phe Gly Thr Phe Ile Phe Gly Ser Ser Met Tyr Asp Phe Arg
                245                 250                 255

Asn Leu Glu Glu Ala Pro Leu Ala Arg Ile Cys Gln Val Val Val Ala
                260                 265                 270

Ala Ile His Lys Arg Asp Lys Asp Leu Pro Cys Asp Ser Ser Val Leu
                275                 280                 285

Tyr Glu Phe Leu Gly Gln Ser Ser Ala Ile Glu Gly Ser Arg Lys Leu
                290                 295                 300

Glu His Thr Thr Gly Leu Lys Phe Phe Asp Arg Ala Ala Met Val Thr
305                 310                 315                 320

Pro Ser Asp Phe Glu Ser Asp Gly Leu Leu Asn Thr Trp Lys Ile Cys
                325                 330                 335

Thr Val Thr Gln Val Glu Glu Leu Lys Ile Leu Ile Arg Met Phe Pro
                340                 345                 350

Val Trp Ala Thr Met Ile Leu Phe Ala Ala Val Leu Asp Asn Met Phe
                355                 360                 365

Ser Thr Phe Ile Glu Gln Gly Met Val Met Glu Lys His Ile Gly Ser
                370                 375                 380

Phe Glu Ile Pro Ala Ala Ser Phe Gln Ser Ile Asp Val Ile Ala Val
385                 390                 395                 400

Leu Ile Leu Val Pro Val Tyr Glu Arg Val Leu Val Pro Val Phe Arg
                405                 410                 415

Lys Phe Thr Gly Arg Ala Asn Gly Ile Thr Pro Leu Gln Arg Met Gly
                420                 425                 430
```

```
Ile Gly Leu Phe Phe Ser Met Leu Ser Met Val Ser Ala Ala Leu Val
            435                 440                 445

Glu Ser Asn Arg Leu Arg Ile Ala Gln Asp Glu Gly Leu Val His Arg
        450                 455                 460

Lys Val Ala Val Pro Met Ser Ile Leu Trp Gln Gly Pro Gln Tyr Phe
465                 470                 475                 480

Leu Ile Gly Val Gly Glu Val Phe Ser Asn Ile Gly Leu Thr Glu Phe
                485                 490                 495

Phe Tyr Gln Glu Ser Pro Asp Ala Met Arg Ser Leu Cys Leu Ala Phe
            500                 505                 510

Ser Leu Ala Asn Val Ser Ala Gly Ser Tyr Leu Ser Ser Phe Ile Val
        515                 520                 525

Ser Leu Val Pro Val Phe Thr Ala Arg Glu Gly Ser Pro Gly Trp Ile
    530                 535                 540

Pro Asp Asn Leu Asn Glu Gly His Leu Asp Arg Phe Phe Trp Met Met
545                 550                 555                 560

Ala Gly Leu Cys Phe Leu Asn Met Leu Ala Phe Val Phe Cys Ala Met
                565                 570                 575

Arg Tyr Lys Cys Lys Lys Ala Ser
            580
```

```
<210> SEQ ID NO 16
<211> LENGTH: 584
<212> TYPE: PRT
<213> ORGANISM: Zea mays
<220> FEATURE:
<221> NAME/KEY: misc_feature
<222> LOCATION: (1)..(584)
<223> OTHER INFORMATION: Ceres CLONE ID no. 352232
<220> FEATURE:
<221> NAME/KEY: misc_feature
<222> LOCATION: (524)..(524)
<223> OTHER INFORMATION: Xaa is any aa, unknown, or other

<400> SEQUENCE: 16

Met Asp Ala Gln Asp Asp Glu Arg Pro Leu Ile Ile His Arg Leu
1               5                   10                  15

Pro Leu Leu Gln Asp Glu Ser Thr Ser Gly Phe Thr Ser Asp Gly Thr
                20                  25                  30

Val Asp Leu Arg Asn Gln Pro Ala Arg Lys Gln Arg Thr Gly Asn Trp
            35                  40                  45

Arg Ala Cys Phe Phe Ile Leu Gly Ala Glu Phe Ala Glu Cys Val Ala
        50                  55                  60

Phe Phe Ala Ile Ser Lys Asn Leu Val Thr Tyr Leu Thr Gly Val Leu
65                  70                  75                  80

His Glu Ser Asn Val Asp Ala Ala Thr Thr Val Ser Thr Trp Ile Gly
                85                  90                  95

Thr Ser Phe Phe Thr Pro Leu Val Gly Ala Phe Leu Ala Asp Thr Phe
                100                 105                 110

Trp Gly Arg Tyr Trp Thr Ile Leu Ala Phe Leu Ser Val Tyr Val Thr
            115                 120                 125

Gly Met Thr Val Leu Thr Ala Ser Ala Leu Leu Pro Leu Leu Met Gly
        130                 135                 140

Ala Ser Tyr Ser Arg Ser Ala His Arg Leu Ser Ala Tyr Leu Gly Leu
145                 150                 155                 160

Tyr Leu Ala Ala Leu Gly Thr Gly Gly Ile Lys Pro Cys Val Cys Ala
                165                 170                 175
```

-continued

```
Leu Gly Ala Asp Gln Phe Asp Ala Ser Asp Pro Val Glu Arg Arg Ala
            180                 185                 190
Lys Gly Ser Phe Phe Asn Trp Tyr Tyr Phe Ser Ile Asn Ile Gly Ser
        195                 200                 205
Leu Leu Ser Ala Thr Val Val Trp Val Gln Asp Asn Val Gly Trp
        210                 215                 220
Gly Val Gly Phe Ala Ile Pro Thr Leu Met Leu Ser Gly Leu Val
225                 230                 235                 240
Leu Phe Val Ala Gly Arg Lys Val Tyr Arg Tyr Gln Arg Val Gly Gly
                245                 250                 255
Ser Pro Leu Thr Arg Ala Ser Gln Val Val Ala Ala Val Arg Asn
            260                 265                 270
Tyr Arg Leu Val Leu Pro Glu Pro Asp Asp Ser Ser Ala Ala Leu Leu
            275                 280                 285
His Gln Ala Pro Pro Gly Thr Thr Glu Gly Asn Tyr Ser Thr Met Gln
            290                 295                 300
His Thr Ser Gln Phe Arg Phe Leu Asp Lys Ala Ala Ile Val Ala Ala
305                 310                 315                 320
Ser Ser Gly Glu Lys Gly Ala Thr Ala Ser Pro Trp Arg Leu Cys Thr
                325                 330                 335
Val Ser Gln Val Glu Glu Leu Lys Thr Val Leu Arg Met Phe Pro Val
            340                 345                 350
Trp Val Ser Met Val Leu Phe Phe Ala Ala Thr Ala Gln Met Ser Ser
            355                 360                 365
Thr Phe Ile Glu Gln Gly Glu Thr Ile Asp Asn Arg Val Gly Pro Phe
        370                 375                 380
Thr Val Pro Pro Ala Ser Leu Ser Thr Phe Asp Val Ile Ser Val Met
385                 390                 395                 400
Val Cys Ile Pro Ile Tyr Asp Lys Ala Leu Val Pro Leu Ala Arg Arg
                405                 410                 415
Ala Thr Gly Lys Glu Arg Gly Leu Ser Gln Leu Gln Arg Leu Gly Val
            420                 425                 430
Gly Leu Ala Leu Ser Val Ala Gly Met Val Tyr Ala Ala Leu Leu Glu
        435                 440                 445
Ala Arg Arg Leu Ser Leu Ala Arg Ala Ala Gly Gly Arg Pro Pro
        450                 455                 460
Met Ser Ile Met Trp Gln Ala Pro Ala Phe Ala Val Leu Gly Ala Gly
465                 470                 475                 480
Glu Val Phe Ala Thr Ile Gly Ile Leu Glu Phe Phe Tyr Asp Gln Ser
                485                 490                 495
Pro Asp Gly Met Lys Ser Leu Gly Thr Ala Leu Ala Gln Leu Ala Val
            500                 505                 510
Ala Ala Gly Asn Tyr Phe Asn Ser Ala Val Leu Xaa Ala Val Ala Ala
        515                 520                 525
Val Thr Thr Arg Asn Gly Glu Ala Gly Trp Ile Pro Asp Asp Leu Asp
        530                 535                 540
Lys Gly His Leu Asp Tyr Phe Phe Trp Phe Met Ala Val Leu Gly Val
545                 550                 555                 560
Val Asn Leu Leu His Phe Leu His Cys Ser Val Arg Tyr Arg Gly Ser
                565                 570                 575
Ser Asn Asn Ser Thr Tyr Ser Ser
            580
```

<210> SEQ ID NO 17
<211> LENGTH: 596
<212> TYPE: PRT
<213> ORGANISM: Prunus persica
<220> FEATURE:
<221> NAME/KEY: misc_feature
<222> LOCATION: (1)..(596)
<223> OTHER INFORMATION: Public GI no. 33411520

<400> SEQUENCE: 17

```
Met Ser Asn Cys Thr Leu Pro Glu Thr Gln Glu Lys Leu Thr Leu Pro
1               5                   10                  15

Asp Ala Trp Asp Phe Lys Gly Arg Pro Ala Glu Arg Ser Lys Thr Gly
            20                  25                  30

Gly Trp Thr Ala Ala Met Ile Leu Gly Gly Glu Ala Cys Glu Arg
        35                  40                  45

Leu Thr Thr Leu Gly Ile Ala Val Asn Leu Val Thr Tyr Leu Thr Gly
    50                  55                  60

Thr Met His Leu Gly Asn Ala Thr Ser Ala Asn Thr Val Thr Asn Phe
65                  70                  75                  80

Leu Gly Thr Ser Phe Met Leu Cys Leu Leu Gly Gly Phe Val Ala Asp
                85                  90                  95

Thr Phe Leu Gly Arg Tyr Leu Thr Ile Ala Ile Phe Ala Thr Phe Gln
            100                 105                 110

Ala Met Gly Val Thr Ile Leu Thr Ile Ser Thr Thr Ile Pro Ser Leu
        115                 120                 125

Arg Pro Pro Lys Cys Thr Ser Asp Thr Ser Thr Pro Cys Ile Pro Ala
    130                 135                 140

Ser Gly Lys Gln Leu Met Val Leu Tyr Ile Ala Leu Tyr Leu Thr Ala
145                 150                 155                 160

Leu Gly Thr Gly Gly Leu Lys Ser Ser Val Ser Gly Phe Gly Ser Asp
                165                 170                 175

Gln Phe Asp Glu Ser Asp Lys Gln Glu Arg Arg Gln Met Thr Asn Phe
            180                 185                 190

Phe Asn Trp Phe Phe Phe Phe Ile Ser Ile Gly Ser Leu Ala Ala Val
        195                 200                 205

Thr Val Leu Val Tyr Ile Gln Asp Asn Leu Gly Arg Gln Trp Gly Tyr
    210                 215                 220

Gly Ile Cys Val Cys Ala Ile Val Leu Gly Leu Ile Val Phe Leu Ser
225                 230                 235                 240

Gly Thr Arg Arg Tyr Arg Phe Lys Lys Leu Val Gly Ser Pro Leu Thr
                245                 250                 255

Gln Ile Ser Gly Val Cys Val Ala Ala Trp Arg Lys Arg Asn Met Glu
            260                 265                 270

Leu Pro Ser Asp Met Ser Phe Leu Tyr Asn Val Asp Asp Ile Asp Asp
        275                 280                 285

Gly Leu Lys Lys Lys Lys Gln Lys Leu Pro His Ser Lys Gln Phe
    290                 295                 300

Arg Phe Leu Asp Lys Ala Ile Lys Glu Pro Lys Thr Thr Ser Gly
305                 310                 315                 320

Thr Ala Met Ile Ile Asn Lys Trp Ser Leu Ser Thr Leu Thr Asp Val
                325                 330                 335

Glu Glu Val Lys Leu Ile Ile Arg Met Leu Pro Ile Trp Ala Thr Thr
            340                 345                 350

Ile Met Phe Trp Thr Val Tyr Ala Gln Met Thr Thr Phe Ser Val Ser
```

```
                355                 360                 365
Gln Ala Thr Ser Met Asp Arg His Ile Gly Lys Ser Phe Gln Ile Pro
    370                 375                 380

Pro Ala Ser Leu Thr Ala Phe Phe Val Gly Ser Ile Leu Leu Thr Val
385                 390                 395                 400

Pro Val Tyr Asp Arg Leu Ile Val Pro Met Ala Arg Lys Ala Leu Glu
                405                 410                 415

Asn Pro Gln Gly Leu Thr Pro Leu Gln Arg Met Gly Val Gly Leu Val
            420                 425                 430

Phe Ser Ile Phe Ala Met Val Ala Ala Leu Thr Glu Val Lys Arg
            435                 440                 445

Leu Asn Ile Ala Arg Ser His Gly Leu Thr Asp Asn Pro Thr Ala Glu
    450                 455                 460

Ile Pro Leu Ser Val Phe Trp Leu Val Pro Gln Phe Phe Val Gly
465                 470                 475                 480

Ser Gly Glu Ala Phe Thr Tyr Ile Gly Gln Leu Asp Phe Phe Leu Arg
                485                 490                 495

Glu Cys Pro Lys Gly Met Lys Thr Met Ser Thr Gly Leu Phe Leu Ser
            500                 505                 510

Thr Leu Ser Leu Gly Phe Phe Phe Ser Ser Leu Leu Val Thr Ile Val
    515                 520                 525

His Lys Thr Thr Gly His Asn Lys Pro Trp Leu Ala Asp Asn Leu Asn
    530                 535                 540

Gln Gly Lys Leu Tyr Asp Phe Tyr Trp Leu Leu Ala Leu Leu Ser Ala
545                 550                 555                 560

Leu Asn Leu Val Ile Tyr Leu Phe Cys Ala Asn Trp Tyr Val Tyr Lys
                565                 570                 575

Asp Lys Arg Leu Ala Glu Glu Gly Ile Glu Leu Glu Glu Pro Glu Ile
            580                 585                 590

Cys Ala His Ala
        595

<210> SEQ ID NO 18
<211> LENGTH: 576
<212> TYPE: PRT
<213> ORGANISM: Oryza sativa (japonica cultivar-group)
<220> FEATURE:
<221> NAME/KEY: misc_feature
<222> LOCATION: (1)..(576)
<223> OTHER INFORMATION: Public GI no. 31429847

<400> SEQUENCE: 18

Met Ala Ala Ile Glu Glu Glu Arg Pro Leu Leu Pro Leu Gln Ser Gln
1               5                   10                  15

Asp Val Gly Ser Glu Tyr Thr Arg Asp Gly Ser Val Asp Ile Asn Lys
            20                  25                  30

Glu Pro Ala Leu Lys His Ser Thr Gly Asn Trp Arg Ala Cys Phe Leu
        35                  40                  45

Ile Leu Gly Val Glu Phe Cys Glu Asn Met Thr Tyr Phe Val Ile Ser
    50                  55                  60

Arg Asn Leu Val Thr Phe Leu Thr Thr Val Leu His Glu Ser Lys Val
65                  70                  75                  80

Asp Ala Ala Arg Asn Val Ser Ala Trp Val Gly Ala Cys Phe Leu Thr
                85                  90                  95

Pro Val Val Gly Ala Phe Leu Ala Asp Thr Tyr Trp Gly Arg Tyr Trp
            100                 105                 110
```

```
Thr Ile Val Val Phe Leu Pro Val Tyr Ile Thr Gly Met Leu Ile Val
        115                 120                 125

Thr Val Ser Ala Ser Leu Pro Met Phe Leu Thr Ser Ser Glu His Gly
        130                 135                 140

Asn Val His Arg Ser Val Val Tyr Leu Gly Leu Tyr Leu Ala Ala Leu
145                 150                 155                 160

Gly Ser Gly Ala Met Lys Pro Cys Thr Ser Ser Phe Gly Ala Asp Gln
                165                 170                 175

Phe Asp Ser Thr Asp Leu Glu Glu Leu Pro Lys Lys Ala Ser Phe Phe
                180                 185                 190

Ser Trp Ser Phe Tyr Met Thr Thr Val Ser Thr Leu Leu Ser Ser Thr
        195                 200                 205

Val Leu Val Trp Leu Gln Asp Asn Val Gly Trp Gly Val Gly Cys Ala
        210                 215                 220

Ile Pro Thr Val Phe Met Ile Ile Ser Phe Pro Val Phe Ile Ala Gly
225                 230                 235                 240

Ser Arg Val Tyr Arg Phe Arg Asn Leu Gly Phe Ser Pro Leu Lys Ser
                245                 250                 255

Leu Cys Gln Val Ile Val Ala Ala Val Arg Lys Cys His Leu Gln Leu
                260                 265                 270

Pro Glu Asn Lys Ser Leu Leu Tyr Glu Pro Ser Asn Ser Ser Ser Thr
        275                 280                 285

Thr Glu Ala Ser His Lys Ile Gln Pro Thr Asn Gln Phe Arg Phe Leu
        290                 295                 300

Asp Lys Ala Ala Ile Val Leu Pro Pro Ser Asp Glu Thr Cys Ile Lys
305                 310                 315                 320

Pro Met Ser Ser Trp Ser Leu Cys Thr Val Thr Gln Val Glu Glu Leu
                325                 330                 335

Lys Met Leu Leu Arg Met Phe Pro Thr Trp Ala Ser Phe Val Ile Phe
                340                 345                 350

Phe Ala Val Asn Gly Gln Met Ser Ser Thr Phe Ile Glu Gln Gly Met
        355                 360                 365

Ala Met Asp Asn His Val Gly Ser Phe Ala Ile Pro Pro Ala Ser Leu
        370                 375                 380

Thr Ile Ile Ala Val Leu Ser Val Leu Val Leu Val Pro Val Tyr Glu
385                 390                 395                 400

Ile Ile Ser Val Pro Leu Val Lys His Phe Thr Gly Gln Asp Lys Gly
                405                 410                 415

Phe Ser His Ala Gln Arg Ile Gly Ile Gly Leu Ser Leu Ser Met Ile
                420                 425                 430

Met Met Val Tyr Ala Ala Leu Leu Glu Met Lys Arg Leu Ala Ile Val
        435                 440                 445

Gln Ser Ser Gly Leu Ala Asp His Asn Val Ala Ala Pro Met Ser Ile
        450                 455                 460

Leu Trp Gln Thr Pro Ala Tyr Phe Leu Gln Gly Val Ser Glu Ile Phe
465                 470                 475                 480

Ser Cys Ile Gly Met Ser Gln Phe Phe Tyr Asp Gln Ala Pro Asp Ser
                485                 490                 495

Met Lys Ser Val Cys Ala Ala Leu Gly Gln Leu Ala Ile Ala Ser Gly
                500                 505                 510

Ala Tyr Phe Asn Thr Phe Val Leu Gly Ala Val Ala Val Ile Thr Thr
        515                 520                 525
```

```
Ser Ser Gly Ala Pro Gly Trp Ile Pro Asp Asn Leu Asn Glu Gly His
    530                 535                 540

Leu Asp Tyr Phe Phe Trp Met Met Ala Thr Leu Ser Leu Leu Asn Leu
545                 550                 555                 560

Ala Met Phe Val Tyr Ser Ser Thr Arg His Arg Glu Asn Thr Ala Ser
                565                 570                 575

<210> SEQ ID NO 19
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 19
```

| | | | | | |
|---|---|---|---|---|---|
| gtgggtaaaa | gtatccttct | ttgtgcattt | ggtattttta | agcatgtaat | aagaaaaacc | 60 |
| aaaatagacg | gctggtattt | aataaaagga | gactaatgta | tgtatagtat | atgatttgtg | 120 |
| tggaatataa | taaagttgta | aaatatagat | gtgaagcgag | tatctatctt | ttgactttca | 180 |
| aaggtgatcg | atcgtgttct | ttgtgatagt | tttggtcgtc | ggtctacaag | tcaacaacca | 240 |
| ccttgaagtt | ttcgcgtctc | ggtttcctct | tcgcatctgg | tatccaatag | catacatata | 300 |
| ccagtgcgga | aaatggcgaa | gactagtggg | cttgaaccat | aaggtttggc | cccaatacgg | 360 |
| attccaaaca | acaagcctag | cgcagtcttt | tgggatgcat | aagactaaac | tgtcgcagtg | 420 |
| atagacgtaa | gatatatcga | cttgattgga | atcgtctaag | ctaataagtt | taccttgacc | 480 |
| gtttatagtt | gcgtcaacgt | ccttatggag | attgatgccc | atcaaataaa | cctgaaaatc | 540 |
| catcaccatg | accaccataa | actcccttgc | tgccgctgct | ttggcttgag | caaggtgttt | 600 |
| ccttgtaaag | ctccgatctt | tggataaagt | gttccacttt | ttgcaagtag | ctctgacccc | 660 |
| tctcagagat | gtcaccggaa | tcttagacag | aacctcctct | gccaaatcac | ttggaagatc | 720 |
| ggacaatgtc | atcatttttg | caggtaattt | ctccttcgtt | gctgctttgg | cttgagcacg | 780 |
| gtgcttcttt | gtaaagctcc | gatctttgga | taagagcgga | tcggaatcct | ctaggaggtg | 840 |
| ccagtccctt | gacctattaa | tttatagaag | gttttagtgt | attttgttcc | aatttcttct | 900 |
| ctaacttaac | aaataacaac | tgcctcatag | tcatgggctt | caaattttat | cgcttggtgt | 960 |
| atttcgttat | ttgcaaggcc | ttggcccatt | ttgagcccaa | taactaaatc | tagccttttc | 1020 |
| agaccggaca | tgaacttcgc | atattggcgt | aactgtgcag | ttttaccttt | ttcggatcag | 1080 |
| acaagatcag | atttagacca | cccaacaata | gtcagtcata | tttgacaacc | taagctagcc | 1140 |
| gacactacta | aaaagcaaac | aaaagaagaa | ttctatgttg | tcattttacc | ggtggcaagt | 1200 |
| ggacccttct | ataaaagagt | aaagagacag | cctgtgtgtg | tataatctct | aattatgttc | 1260 |
| accgacacaa | tcacacaaac | ccttctctaa | tcacacaact | tcttcatgat | ttacgacatt | 1320 |
| aattatcatt | aactctttaa | attcacttta | catgctcaaa | aatatctaat | ttgcagcatt | 1380 |
| aatttgagta | ccgataacta | ttattataat | cgtcgtgatt | cgcaatcttc | ttcattagat | 1440 |
| gctgtcaagt | tgtactcgca | cgcggtggtc | cagtgaagca | aatccaacgg | tttaaaacct | 1500 |
| tcttacattt | ctagatctaa | tctgaaccgt | cagatatcta | gatctcattg | tctgaacaca | 1560 |
| gttagatgaa | actgggaatg | aatctggacg | aaattacgat | cttacaccaa | cccctcgac | 1620 |
| gagctcgtat | atataaagct | tatacgctcc | tccttcacct | tcgtactact | actaccacca | 1680 |
| catttcttta | gctcaacctt | cattactaat | ctccttttaa | ggtatgttca | cttttcttcg | 1740 |

| attcatactt tctcaagatt cctgcatttc tgtagaattt gaaccaagtg tcgattttg | 1800 |
| tttgagagaa gtgttgattt atagatctgg ttattgaatc tagattccaa tttttaattg | 1860 |
| attcgagttt gttatgtgtg tttatactac ttctcattga tcttgtttga tttctctgct | 1920 |
| ctgtattagg tttctttcgt gaatcagatc ggaa | 1954 |

```
<210> SEQ ID NO 20
<211> LENGTH: 881
<212> TYPE: DNA
<213> ORGANISM: Arabidopsis thaliana
<220> FEATURE:
<221> NAME/KEY: misc_feature
<222> LOCATION: (1)..(881)
<223> OTHER INFORMATION: Ceres Promoter YP0144

<400> SEQUENCE: 20
```

| ggaaagaagc ggtttatgcg ctgcgcataa cactattatg tctcgggaga acaaagatgg | 60 |
| aagcaagagc ggtttgattg gaccgggact ctttagtggc cttgtttttg gctctacttc | 120 |
| tgatcattct cagtctggag ctagcgctgt ctctgattgt actgattctg ttgaacgaat | 180 |
| acagtttgag aataggcaga agaacaagaa gatgatgata ccgatgcagg ttctagtacc | 240 |
| ttcatcaatg aaatctccaa gtaattcaca tgaaggagaa acaaacatct atgacttcat | 300 |
| ggttccggag gagagagttc acggcggtgg gctagtaatg tctttacttg gtggctccat | 360 |
| tgatcgaaac tgaaagccat ttatggtaaa agtgtcacat tctcagcaaa aacctgtgta | 420 |
| aagctgtaaa atgtgtggga atctccgaat ctgtttgtag ccggttacgt tatgctggat | 480 |
| caaaaactca agatttgttg gatattgtta tgctggatcg gtggtgaaac cacttcccgg | 540 |
| ttgctaaata aataaacgtt tttgttttat aatctttttc actaaacggc agtatgggcc | 600 |
| tttagtgggc ttcctttaag cgaccaatac aatcgtcgca ccggaatcta ctaccattta | 660 |
| taggtttatt catgtaaaac ctcggaaaat ttgagagcca caacggtcaa gagacaaaaa | 720 |
| caacttgaag ataaagggat aaggaaggct tcctacatga tggacaacat ttctttccac | 780 |
| acaaattctc ataataaaaa tcttataata caaatactta cgtcataatc attcaatcta | 840 |
| gtccccatgt tttaaggtcc tgtttcttgt ctgatacaaa t | 881 |

```
<210> SEQ ID NO 21
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190

<400> SEQUENCE: 21
```

| taaatagtga cattggtaag aagaaaaaaa acactattaa atagtgaaaa aatggtttat | 60 |
| aactctctta attaacatta cttattattg ctagcaccta aaatctccca caaaatattt | 120 |
| gttgtaaaac acaaatttac aaaatgattt tgttttaaa ttagtaacac atgttcatat | 180 |
| atacgttaat aagaacatac cctatatgat tttataaaa aaatttctt tgagacgtct | 240 |
| tattcttttt tctttaataa tatgcaattg tgagagtttg gatttgaatg gtagcattag | 300 |
| aagcaaactt gaaccaaaca tatttcatga agtcaaactt gaaccaatgt gatcactaat | 360 |
| cacagtgttc gcagtgtaag gcatcagaaa atagaagaag ggacatagct atgaatcata | 420 |
| taatcttgac acatgtttta taggtttag gtgtgtatgc taacaaaaaa tgagacagct | 480 |
| ttcttctaat agacttaata tttgggctaa atgtaccaca gttgtgaatt tcttacaaaa | 540 |

```
atgggccgag ctacaaaaaa ctacaggccc actctcaact cttatcaaac gacagcgttt     600 tacttttta aaagcacaca cttttgttt ggtgtcggtg acggtgagtt tcgtccgctc       660
ttcctttaaa ttgaagcaac ggttttgatc cgatcaaatc caacggtgct gattacacaa    720
agcccgagac gaaaacgttg actattaagt taggttttaa tctcagccgt taatctacaa    780
atcaacggtt ccctgtaaaa cgaatcttcc ttccttcttc acttccgcgt cttctctctc    840
aatcacctca aaaaatcga tttcatcaaa atattcaccc gcccgaattt gactctccga     900
tcatcgtctc cgaatctaga tcgacgagat caaaaccccta gaaatctaaa tcggaatgag   960
aaattgattt tgatacgaat tagggatctg tgtgttgagg ac                       1002
```

<210> SEQ ID NO 22
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 22

```
tttcgatcct cttcttttt aggtttcttg atttgatgat cgccgccagt agagccgtcg       60
tcggaagttt cagagattaa aaccatcacc gtgtgagttg gtagcgaatt aacggaaagt     120
ctaagtcaag attttttaaa aagaaattta tgtgtgaaaa gaagccgttg tgtatattta    180
tataatttag aaaatgtttc atcatttaa ttaaaaaatt ataatttgt agaagaaga       240 agcatttttt atacataaat catttacctt ctttactgtg ttttcttca cttacttcat    300 ttttactttt ttacaaaaaa gtgaaaagta aattacgtaa ttggtaacat aaattcactt   360
taaatttgca tatgttttgt ttcttcgga aactatatcg aaaagcaaac ggaaagaact     420 tcacaaaaa ccctagctaa ctaaagacgc atgtgttctt cttattcttc atatatcctc     480
tgtttcttgt gttctgtttt gagtcttaca ttttcaatat ctgactctga ttactatatc    540
taaaagggaa catgaagaac ttgagaccat gttaaactgt acaatgcctt caaacatggc    600
taactaaaga tacattagat ggctttacag tgtgtaatgc ttattatctt taggttttt     660 aaatcccttg tattaagtta tttaccaaat tatgttcttg tactgcttat tggcttggtt    720
gttgtgtgct ttgtaaacaa cacctttggc tttatttcat cctttgtaaa cctactggtc   780
tttgttcagc tcctcttgga agtgagttg tatgcctgga acgggttta atggagtgtt    840 tatcgacaaa aaaaaatgt agcttttgaa atcacagaga gtagttttat attcaaatta    900
catgcatgca actaagtagc aacaagttg atatggccga gttggtctaa ggcgccagat    960
taaggttctg gtccgaaagg gcgtgggttc aaatcccact gtcaacattc tctttttctc  1020
aaattaatat ttttctgcct caatggttca ggcccaatta tactagacta ctatcgcgac   1080
taaaataggg actagccgaa ttgatccggc ccagtatcag ttgtgtatca ccacgttatt   1140
tcaaatttca aactaaggga taaagatgtc atttgacata tgagatattt ttttgctcca   1200
ctgagatatt tttctttgtc ccaagataaa atatctttc tcgcatcgtc gtctttccat    1260
ttgcgcatta aaccaaaaag tgtcacgtga tatgtcccca accactacga atttaacta   1320 cagatttaac catggttaaa ccagaattca cgtaaaccga ctctaaaccct agaaaatatc  1380 taaaccttgg ttaatatctc agccccctta taaataacga gacttcgtct acatcgttct   1440
acacatctca ctgctcacta ctctcactgt aatcccttag atcttcttt caaatttcac   1500
```
cattgcactg gatg                                                           1514

<210> SEQ ID NO 23
<211> LENGTH: 1026
<212> TYPE: DNA
<213> ORGANISM: Arabidopsis thaliana
<220> FEATURE:
<221> NAME/KEY: misc_feature
<222> LOCATION: (1)..(1026)
<223> OTHER INFORMATION: Ceres Promoter YP0050

<400> SEQUENCE: 23
aatctgatct ctagtccagt cgattggtac ttgagggaaa catcatattt ttaaaccttg      60
tctcagtaag ctaacacaca ccccttgtga ttacttatcc atgtttatcc acaagaatgc     120
agttggattg agatattttc ttctttgttg aaatcaggcc tcaaggtgtt catgtggtct     180
gcaaaaaaat tcccaaaaat aaagatagtg acatctgaaa tcgataatgg attagacgaa     240
gagtttcgtg ttattccttg gtatgggcgg gtttggggac agatattttg gcacagacga     300
ggactaggcc actgtggtcc tgcagcatta ggtgtccctt ccatgtcctg cattacattt     360
tattgatgga ttcatcaccc tatctactac aacggctaca caaactatga agagttttgt     420
ttactaataa atgcccaagt gaggggtcga tcgaacccgg gacacgtttt tcagtttacc     480
atatagaatt atccttggaa cccttgatac tccatagaac atcaccacct ctgttgtcat     540
ctcaggaatc caggttcaaa cctagtctct ctctccctag tgggaggtat atggccactg     600
ggccaatgat gacaaaatgc aaaaaaaata aaatacattt gggttcatta tctaaaatat     660
ctcttgtgtt tgtaagtttt ggttgcacac tcgtgtggtt gaagtgtgtg tgagaggtac     720
tatacaatac actctgcttt tgttttgtac ctatctcttt ctcttctcca catatccaag     780
actttgggga taaagctgag atcattggtt gccatttggt tgtgtagaag caatcaccca     840
tttgctttat ccgaggttga taaatttcct cgggttctcc ttctgacacg tatgacaaat     900
tctaatagta tattcctcgt agatattacc tatatattct caatagttgc aggtacttaa     960
ggctttgtct tggcatcctc gtcctcttca gcaaaactcg tctctcttgc actccaaaaa    1020
gcaacc                                                                1026

<210> SEQ ID NO 24
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 24
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcccttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540

```
ttgaacgctt tccggttatg accaatttgt tgtagctcct tgtaagtaga acttactggg      600
accagcgaga cagtttatgt gaatgttcat gcttaagtgt cgaacgtatc tatctctact      660
atagctctgt agtcttgtta dacagttagt tttatatctc cattttttg tagtcttgct       720 agttgagata ttacctcttc tcttcaaagt atccttgaac gctcaccggt tatgaaatct      780
ctacactata gctctgtagt cttgctagat agttagttct ttagctctct ttttgtagcc      840 tagttctta gctctccttt tgtagccttg ctacagagta agatgggata ttacctcctt      900
gaacgctctc cggttatgac caatttgttg tagctccttg taagtagaac ttaggataga     960
gtgagtcaac tttaagaaag aacctagtat gtggcataac cagattgcag gctctgtctc     1020
ggctacagta acgtaactct atagctcttt gttttgttca gaaagaacca gtgattggat     1080
gattcgtcct tagaaactgg acctaacaac agtcattggc tttgaaatca agccacaaca    1140
atgcctatat gaaccgtcca tttcatttat ccgtttcaaa ccagcccatt acatttcgtc     1200
ccattgataa ccaaaagcgg ttcaatcaga ttatgtttta attttaccaa attctttatg     1260
aagtttaaat tatactcaca ttaaaaggat tattggataa tgtaaaaatt ctgaacaatt     1320
actgattttg gaaaattaac aaatattctt tgaaatagaa gaaaaagcct ttttcctttt     1380
gacaacaaca tataaaatca tactcccatt aaaaagattt taatgtaaaa ttctgaatat    1440
aagatatttt ttacaacaac aaccaaaaat atttattttt ttccttttt acagcaacaa      1500 gaaggaaaaa ctttttttt tgtcaagaaa aggggagatt atgtaaacag ataaaacagg      1560
gaaaataact aaccgaactc tcttaattaa catcttcaaa taaggaaaat tatgatccgc     1620
atatttagga agatcaatgc attaaaacaa cttgcacgtg gaaagagaga ctatacgctc    1680
cacacaagtt gcactaatgg tacctctcac aaaccaatca aaatactgaa taatgccaac     1740
gtgtacaaat tagggtttta cctcacaacc atcgaacatt ctcgaaacat tttaaacagc    1800
ctggcgccat agatctaaac tctcatcgac caattttga ccgtccgatg gaaactctag    1860
cctcaaccca aaactctata taagaaatc ttttccttcg ttattgctta ccaaatacaa     1920
accctagccg ccttattcgt cttcttcgtt ctctagtttt ttcctcagtc tctgttctta    1980
gatcccttgt agtttccaaa tcttccgata aggcct                              2016
```

<210> SEQ ID NO 25
<211> LENGTH: 1823
<212> TYPE: DNA
<213> ORGANISM: Arabidopsis thaliana
<220> FEATURE:
<221> NAME/KEY: misc_feature
<222> LOCATION: (1)..(1823)
<223> OTHER INFORMATION: Ceres Promoter 21876

<400> SEQUENCE: 25

```
gtctcttaaa aaggatgaac aaacacgaaa ctggtggatt atacaaatgt cgccttatac      60
atatatcggt tattggccaa aagagctatt ttaccttatg gataatggtg ctactatggt      120
tggagttgga ggtgtagttc aggcttcacc ttctggttta agccctccaa tgggtaatgg     180
taaatttccg gcaaaaggtc ctttgagatc agccatgttt tccaatgttg aggtcttata     240
ttccaagtat gagaaaggta aaataaatgc gtttcctata gtggagttgc tagatagtag     300
tagatgttat gggctacgaa ttggtaagag agttcgattt tggactagtc cactcggata     360 cttttttcaat tatggtggtc ctggaggaat ctccttgtgga gtttgatatt tgcgagtata   420
atctttgaac ttgtgtagat tgtacccaaa accgaaaaca tatcctatat aaatttcatt     480
```

```
atgagagtaa aattgtttgt tttatgtatc atttctcaac tgtgattgag ttgactattg   540
aaaacatatc ttagataagt ttcgttatga gagttaatga tgattgatga catacacact   600
cctttatgat ggtgattcaa cgttttggag aaaatttatt tataatctct cataaattct   660
ccgttattag ttgaataaaa tcttaaatgt ctcctttaac catagcaaac caacttaaaa   720
atttagattt taaagttaag atggatattg tgattcaacg attaattatc gtaatgcata   780
ttgattatgt aaaataaaat ctaactaccg gaatttattc aataactcca ttgtgtgact   840
gcatttaaat atatgtttta tgtcccatta attaggctgt aatttcgatt tatcaattta   900
tatactagta ttaatttaat tccatagatt tatcaaagcc aactcatgac ggctagggtt   960
ttccgtcacc ttttcgatca tcaagagagt ttttttataa aaaaatttat acaattatac  1020
aatttcttaa ccaaacaaca cataattata agctatttaa catttcaaat tgaaaaaaaa  1080
aatgtatgag aattttgtgg atccattttt gtaattcttt gttgggtaaa ttcacaacca  1140
aaaaaataga aaggcccaaa acgcgtaagg gcaaattagt aaaagtagaa ccacaaagag  1200
aaagcgaaaa ccctagacac ctcgtagcta taagtaccct cgagtcgacc aggattaggg  1260
tgcgctctca tatttctcac attttcgtag ccgcaagact cctttcagat tcttacttgc  1320
aggttagata ttttctctct ttagtgtctc cgatcttcat cttcttatga ttattgtagc  1380
tgtttagggt ttagattctt agtttttagct ctatattgac tgtgattatc gcttattctt  1440
tgctgttgtt atactgcttt tgattctcta gctttagatc cgtttactcg tcgatcaata  1500
ttgttcctat tgagtctgat gtataatcct ctgattaatt gatagcgttt agttttgata  1560
tcgtcttcgc atgttttttta tcatgtcgat ctgtatctgc tctggttata gttgattctg  1620
atgtatttgg ttggtgatgt tccttagatt tgatatacct gttgtctcgt ggtttgatat  1680
gatagctcaa ctggtgatat gtggttttgt ttcagtggat ctgtgtttga ttatattgtt  1740
gacgttttgg ttgttgtatg gttgatggtt gatgtatttt tgttgattct gatgtttcga  1800
tttttgtttt tgttttgaca gct                                         1823
```

MODULATING PLANT NITROGEN LEVELS

CROSS-REFERENCE TO RELATED APPLICATIONS

This application claims priority under 35 U.S.C. § 119 to U.S. Provisional Application No. 60/637,311, filed Dec. 16, 2004, and to U.S. Provisional Application No. 60/705,119, filed Aug. 2, 2005, both of which are incorporated herein by reference in their entireties.

TECHNICAL FIELD

This document provides methods and materials related to modulating (e.g., increasing or decreasing) nitrogen levels in plants. For example, this document provides plants having increased nitrogen levels as well as materials and methods for making plants and plant products having increased nitrogen levels.

BACKGROUND

The photoautotrophic production of organic nitrogenous compounds is crucial to plant metabolism, growth, and development. Protein and amino acid contents of harvested plant materials are of great agronomic importance in many crop species. Light-driven nitrogen (N) assimilation in leaves has evolved to operate alongside and integrate with photosynthesis and respiration. The production of reduced carbon (C) in photosynthesis and its reoxidation in respiration are necessary to produce both the energy and C skeletons required for the incorporation of inorganic N into amino acids. Conversely, N assimilation is required to sustain the output of organic C and N. This network is further complicated by the concomitant operation of photorespiratory metabolism. Both the rate of N assimilation and the coordination of C and N assimilation are under multifactorial control by a repertoire of signals, which provide information on C and N status. There is a need for compositions and methods that can increase nitrogen content in plants under varying nitrogen conditions.

SUMMARY

This document provides methods and materials related to plants having modulated (e.g., increased or decreased) nitrogen content. For example, this document provides transgenic plants and plant cells having increased levels of nitrogen, nucleic acids used to generate transgenic plants and plant cells having increased levels of nitrogen, and methods for making plants and plant cells having increased levels of nitrogen. Such plants and plant cells can be grown to produce seeds having increased nitrogen content. The seeds may be used to produce foodstuffs and animal feed having increased nutritional (e.g., protein) content, which may benefit both food producers and consumers. While not being bound to any particular mode of action, the nitrogen-modulating polypeptides provided herein may have activities as transport proteins. For example, the polypeptides provided herein may be involved in transport of nitrogen, e.g., organic nitrogen in the form of peptides or amino acids, or inorganic nitrogen in the form of ammonium or nitrate.

In one embodiment, a method of modulating the level of nitrogen in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NO:2, SEQ ID NOs:4-18, and the consensus sequence set forth in FIG. 1 (SEQ ID NOs:26-54), where a tissue of a plant produced from the plant cell has a difference in the level of nitrogen as compared to the corresponding level in tissue of a control plant that does not comprise the nucleic acid.

In another embodiment, a method of modulating the level of nitrogen in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, SEQ ID NO:16, and the consensus sequence set forth in FIG. 1 (SEQ ID NOs: 26-54), where a tissue of a plant produced from the plant cell has a difference in the level of nitrogen as compared to the corresponding level in tissue of a control plant that does not comprise the nucleic acid.

In a further embodiment, a method of modulating the level of nitrogen in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, and SEQ ID NO:16, where a tissue of a plant produced from the plant cell has a difference in the level of nitrogen as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:4. The nucleotide sequence can encode a polypeptide comprising an amino acid sequence corresponding to the consensus sequence set forth in FIG. 1 (SEQ ID NOs:26-54). The difference can be an increase in the level of nitrogen.

The isolated nucleic acid can be operably linked to a regulatory region. The regulatory region can be a tissue-specific regulatory region. The tissue-specific regulatory region can be a promoter. The promoter can be selected from the group consisting of YP0092 (SEQ ID NO:55), PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672 (SEQ ID NO:57), PT0678, PT0688, PT0837 (SEQ ID NO:56), YP0128, YP0275, PT0625, PT0660, PT0683, and PT0758. The regulatory region can be a broadly expressing promoter. The broadly expressing promoter can be selected from the group consisting of p13879, p32449, 21876, p326, YP0158, YP0214, YP0380, PT0848, PT0633, YP0050, YP0144, and YP0190. The regulatory region can be an inducible promoter.

The plant can be a dicot. The plant can be a member of the genus *Brassica, Glycine, Gossypium, Helianthus, Lactuca, Lycopersicon, Solanum, Vitis, Pisum, Medicago, Carthamus, Arachis, Olea, Linum,* or *Trifolium*. The plant can be a monocot. The plant can be a member of the genus *Zea,*

Triticum, Hordeum, Secale, Oryza, Triticosecale, Avena, Musa, Elaeis, Phleum, or Sorghum. The tissue can be seed tissue.

A method of producing a plant tissue is also provided. The method comprises growing a plant cell comprising an isolated nucleic acid comprising a nucleotide sequence encoding a polypeptide having 80 percent or greater sequence identity to an amino acid sequence selected from the group consisting of SEQ ID NO:2, SEQ ID NOs:4-18, and the consensus sequence set forth in FIG. 1 (SEQ ID NOs:26-54), where the tissue has a difference in the level of nitrogen as compared to the corresponding level in tissue of a control plant that does not comprise the nucleic acid.

In another embodiment, a method of producing a plant tissue is provided. The method comprises growing a plant cell comprising an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, SEQ ID NO:16, and the consensus sequence set forth in FIG. 1 (SEQ ID NOs:26-54), where the tissue has a difference in the level of nitrogen as compared to the corresponding level in tissue of a control plant that does not comprise the nucleic acid.

In yet another embodiment, a method of producing a plant tissue is provided. The method comprises growing a plant cell comprising an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, and SEQ ID NO:16, where the tissue has a difference in the level of nitrogen as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:4. The nucleotide sequence can encode a polypeptide comprising an amino acid sequence corresponding to the consensus sequence set forth in FIG. 1 (SEQ ID NOs:26-54). The difference can be an increase in the level of nitrogen.

The isolated nucleic acid can be operably linked to a regulatory region. The regulatory region can be a tissue-specific regulatory region. The tissue-specific regulatory region can be a promoter. The promoter can be selected from the group consisting of YP0092 (SEQ ID NO: 55), PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672 (SEQ ID NO:57), PT0678, PT0688, PT0837 (SEQ ID NO:56), YP0128, YP0275, PT0625, PT0660, PT0683, and PT0758. The regulatory region can be a broadly expressing promoter. The broadly expressing promoter can be selected from the group consisting of p13879, p132449, 21876, p326, YP0158, YP0214, YP0380, PT0848, PT0633, YP0050, YP0144, and YP0190. The regulatory region can be an inducible promoter.

The plant tissue can be dicotyledonous. The plant tissue can be a member of the genus Brassica, Glycine, Gossypium, Helianthus, Lactuca, Lycopersicon, Solanum, Vitis, Pisum, Medicago, Carthamus, Arachis, Olea, Linum, or Trifolium. The plant tissue can be monocotyledonous. The plant tissue can be a member of the genus Zea, Triticum, Hordeum, Secale, Oryza, Triticosecale, Avena, Musa, Elaeis, Phleum, or Sorghum. The tissue can be seed tissue.

A plant cell is also provided. The plant cell comprises an isolated nucleic acid comprising a nucleotide sequence encoding a polypeptide having 80 percent or greater sequence identity to an amino acid sequence selected from the group consisting of SEQ ID NO:2, SEQ ID NOs:4-18, and the consensus sequence set forth in FIG. 1 (SEQ ID NOs:26-54), where a tissue of a plant produced from the plant cell has a difference in the level of nitrogen as compared to the corresponding level in tissue of a control plant that does not comprise the nucleic acid.

In another embodiment, a plant cell is provided. The plant cell comprises an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, SEQ ID NO:16, and the consensus sequence set forth in FIG. 1 (SEQ ID NOs:26-54), where a tissue of a plant produced from the plant cell has a difference in the level of nitrogen as compared to the corresponding level in tissue of a control plant that does not comprise the nucleic acid.

In yet another embodiment, a plant cell is provided. The plant cell comprises an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:5, and SEQ ID NO:16, where a tissue of a plant produced from the plant cell has a difference in the level of nitrogen as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:4. The nucleotide sequence can encode a polypeptide comprising an amino acid sequence corresponding to the consensus sequence set forth in FIG. 1 (SEQ ID NOs:26-54). The difference can be an increase in the level of nitrogen.

The isolated nucleic acid can be operably linked to a regulatory region. The regulatory region can be a tissue-specific regulatory region. The tissue-specific regulatory region can be a promoter. The promoter can be selected from the group consisting of YP0092 (SEQ ID NO: 55), PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672 (SEQ ID NO:57), PT0678, PT0688, PT0837 (SEQ ID NO: 56), YP0128, YP0275, PT0625, PT0660, PT0683, and PT0758. The regulatory region can be a broadly expressing promoter. The broadly expressing promoter can be selected from the group consisting of p13879, p32449, 21876, p326, YP0158, YP0214, YP0380, PT0848, PT0633, YP0050, YP0144, and YP0190. The regulatory region can be an inducible promoter.

The plant can be a dicot. The plant can be a member of the genus *Brassica, Glycine, Gossypium, Helianthus, Lactuca, Lycopersicon, Solanum, Vitis, Pisum, Medicago, Carthamus, Arachis, Olea, Linum*, or *Trifolium*. The plant can be a monocot. The plant can be a member of the genus *Zea, Triticum, Hordeum, Secale, Oryza, Triticosecale, Avena, Musa, Elaeis, Phleum*, or *Sorghum*. The tissue can be seed tissue.

A transgenic plant is also provided. The transgenic plant comprises any of the plant cells described above. Progeny of the transgenic plant are also provided. The progeny have a difference in the level of nitrogen as compared to the level of nitrogen in a corresponding control plant that does not comprise the isolated nucleic acid. Seed and vegetative tissue from the transgenic plant are also provided. In addition, food products and feed products comprising vegetative tissue from the transgenic plant are provided.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
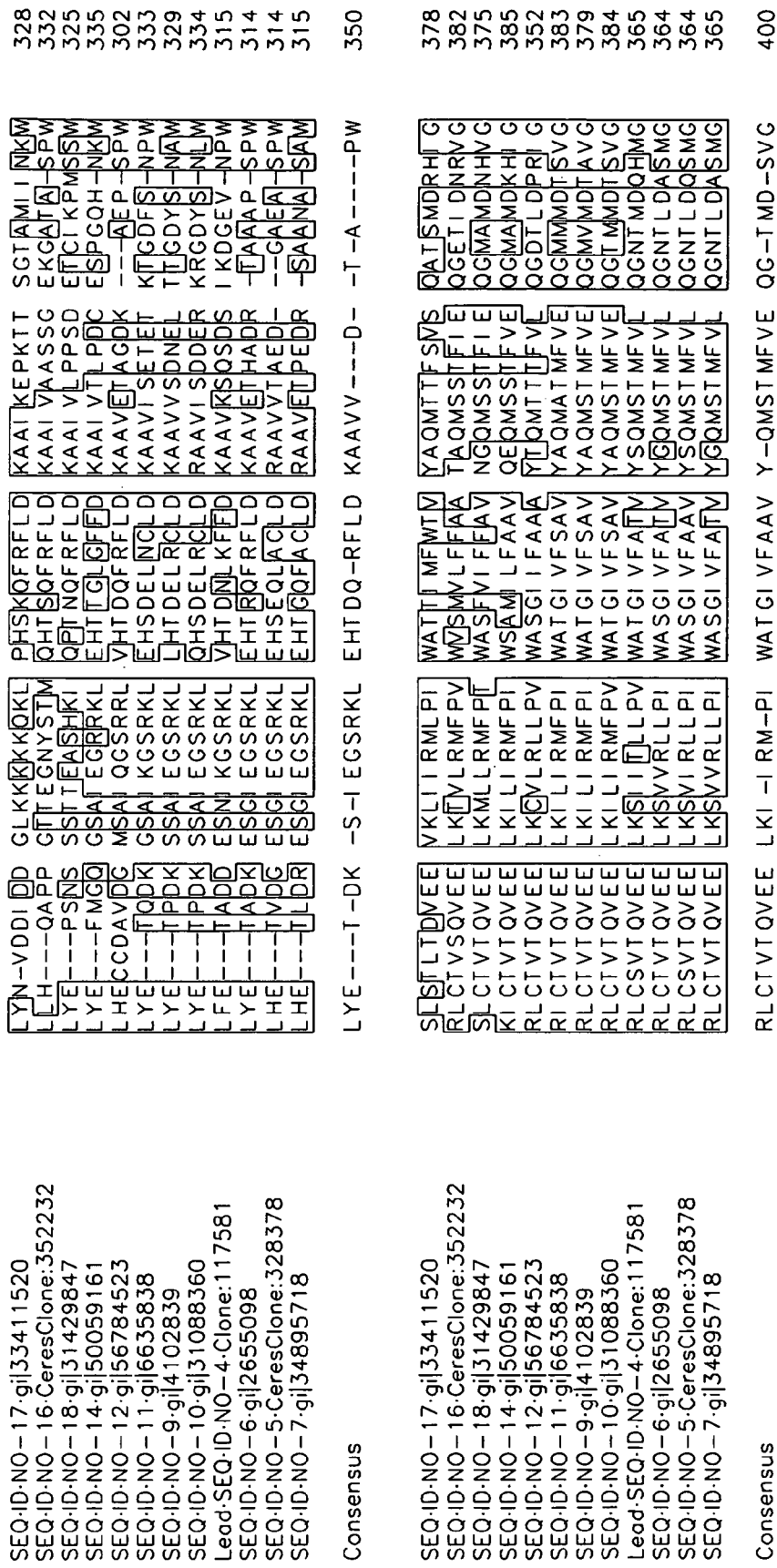
FIG. 1 is an alignment of SEQ ID NO:4 with orthologous amino acid sequences SEQ ID NOs:5-7, SEQ ID NOs:9-12, SEQ ID NO:14, and SEQ ID NOs:16-18. The consensus sequence (SEQ ID NOs:26-54) determined by the alignment is set forth.

This invention features methods and materials related to plants, plant products, plant tissues, and plant cells having modulated (e.g., increased or decreased) levels of nitrogen. For example, this document provides plants and plant cells having increased nitrogen levels as well as methods for producing such plants and plant cells. The methods can include transforming a plant cell with a nucleic acid encoding a nitrogen-modulating polypeptide, wherein expression of the polypeptide results in increased levels of nitrogen. Plants and plant cells produced using such methods can be grown to produce seeds having increased nitrogen levels. The seeds may be used to produce foodstuffs and animal feed having increased nutritional (e.g., protein) content, which may benefit both food producers and consumers.

Polypeptides

The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

Described herein are nitrogen-modulating polypeptides. Nitrogen-modulating polypeptides can be effective to modulate nitrogen levels when expressed in a plant or plant cell. Modulation of the level of nitrogen can be either an increase or a decrease in the level of nitrogen relative to the corresponding level in a control plant. A nitrogen-modulating polypeptide can be a transporter polypeptide, such as an oligopeptide transporter polypeptide.

A nitrogen-modulating polypeptide can be a proton-dependent oligopeptide transport (POT) family polypeptide. POT family polypeptides are reported to be involved in the intake of small peptides with the concomitant uptake of a proton. SEQ ID NO:2 and SEQ ID NO:4 set forth the amino acid sequences of *Arabidopsis* clones, identified herein as Ceres cDNA ID 2998984 and Ceres clone 117581 (SEQ ID NO:3), respectively, each of which has a PTR2 domain characteristic of a peptide transporter polypeptide.

A nitrogen-modulating polypeptide can comprise the amino acid sequence set forth in SEQ ID NO:2 or SEQ ID NO:4. Alternatively, a nitrogen-modulating polypeptide can be a homolog, ortholog, or variant of the polypeptide having the amino acid sequence set forth in SEQ ID NO:2 or SEQ ID NO:4. For example, a nitrogen-modulating polypeptide can have an amino acid sequence with at least 40% sequence identity, e.g., 41%, 45%, 47%, 48%, 49%, 50%, 51%, 52%, 56%, 57%, 60%, 61%, 62%, 63%, 64%, 65%, 67%, 68%, 70%, 75%, 80%, 85%, 90%, 95%, 97%, 98%, or 99% sequence identity, to the amino acid sequence set forth in SEQ ID NO:2 or SEQ ID NO:4. In some embodiments, a nitrogen-modulating polypeptide comprises an amino acid sequence with at least 40% sequence identity to SEQ ID NO:2 and a chloroplast targeting signal sequence at the N-terminus of the polypeptide.

Amino acid sequences of orthologs of the polypeptide having the amino acid sequence set forth in SEQ ID NO:4 are provided in FIG. 1, along with a consensus sequence (SEQ ID NOs:26-54). A consensus amino acid sequence (SEQ ID NOs:26-54) for such orthologs was determined by aligning amino acid sequences, e.g., amino acid sequences related to SEQ ID NO:4, from a variety of species and determining the most common amino acid or type of amino acid at each position. For example, the alignment in FIG. 1 provides the amino acid sequences of Ceres clone 117581 (SEQ ID NO:4), CeresClone:328378 (SEQ ID NO:5), gi|2655098 (SEQ ID NO:6), gi|34895718 (SEQ ID NO:7), gi|4102839 (SEQ ID NO:9), gi|31088360 (SEQ ID NO:10), gi|6635838 (SEQ ID NO:11), gi|56784523 (SEQ ID NO:12), gi|50059161 (SEQ ID NO:14), CeresClone:352232 (SEQ ID NO:16), gi|33411520 (SEQ ID NO:17), and gi|31429847 (SEQ ID NO:18). Other orthologs include gi|50933627 (SEQ ID NO:8), gi|56784524 (SEQ ID NO:13), and gi|6409176 (SEQ ID NO:15).

In some cases, a nitrogen-modulating polypeptide can include a polypeptide having at least 80% sequence identity (e.g., 80%, 85%, 90%, 93%, 95%, 97%, 98%, or 99% sequence identity) to an amino acid sequence corresponding to SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or the consensus sequence set forth in FIG. 1 (SEQ ID NOs:26-54).

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given nitrogen-modulating polypeptide can be modified such that optimal expression in a particular plant species is obtained, using appropriate codon bias tables for that species.

A nitrogen-modulating polypeptide encoded by a recombinant nucleic acid can be a native nitrogen-modulating polypeptide, i.e., one or more additional copies of the coding sequence for a nitrogen-modulating polypeptide that is naturally present in the cell. Alternatively, a nitrogen-modulating polypeptide can be heterologous to the cell, e.g., a transgenic *Lycopersicon* plant can contain the coding sequence for a transporter polypeptide from a *Glycine* plant.

A nitrogen-modulating polypeptide can include additional amino acids that are not involved in nitrogen modulation, and thus can be longer than would otherwise be the case. For example, a nitrogen-modulating polypeptide can include an amino acid sequence that functions as a reporter. Such a nitrogen-modulating polypeptide can be a fusion protein in which a green fluorescent protein (GFP) polypeptide is fused to SEQ ID NO:2, or in which a yellow fluorescent protein (YFP) polypeptide is fused to SEQ ID NO:4. In some embodiments, a nitrogen-modulating polypeptide includes a purification tag or a leader sequence added to the amino or carboxy terminus.

Nitrogen-modulating polypeptide candidates suitable for use in the invention can be identified by analysis of nucleotide and polypeptide sequence alignments. For example, performing a query on a database of nucleotide or polypeptide sequences can identify orthologs of nitrogen-modulating polypeptides. Sequence analysis can involve BLAST, Reciprocal BLAST, or PSI-BLAST analysis of nonredundant databases using known nitrogen-modulating polypeptide amino acid sequences. Those proteins in the database that have greater than 40% sequence identity can be identified as candidates for further evaluation for suitability as a nitrogen-modulating polypeptide. If desired, manual inspection of such candidates can be carried out in order to narrow the number of candidates to be further evaluated. Manual inspection can be performed by selecting those candidates that appear to have domains suspected of being present in nitrogen-modulating polypeptides, e.g., conserved functional domains.

The identification of conserved regions in a template or subject polypeptide can facilitate production of variants of wild type nitrogen-modulating polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam and genome.wustl.edu/Pfam. A description of the information included at the Pfam database is described in Sonnhammer et al., 1998, *Nucl. Acids Res.* 26: 320-322; Sonnhammer et al., 1997, *Proteins* 28:405-420; and Bateman et al., 1999, *Nucl. Acids Res.* 27:260-262.

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

Typically, polypeptides that exhibit at least about 40% amino acid sequence identity are useful to identify conserved regions. Conserved regions of related polypeptides can exhibit at least 45% amino acid sequence identity (e.g., at least 50%, at least 60%, at least 70%, at least 80%, or at least 90% amino acid sequence identity). In some embodiments, a conserved region of target and template polypeptides exhibit at least 92, 94, 96, 98, or 99% amino acid sequence identity. Amino acid sequence identity can be deduced from amino acid or nucleotide sequences. In certain cases, highly conserved domains have been identified within nitrogen-modulating polypeptides. These conserved regions can be useful in identifying functionally similar (orthologous) nitrogen-modulating polypeptides.

In some instances, suitable nitrogen-modulating polypeptides can be synthesized on the basis of consensus functional domains and/or conserved regions in polypeptides that are homologous nitrogen-modulating polypeptides. Domains are groups of substantially contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Consensus domains and conserved regions can be identified by homologous polypeptide sequence analysis as described above. The suitability of polypeptides for use as nitrogen-modulating polypeptides can be evaluated by functional complementation studies.

Nucleic Acids

Isolated nucleic acids are provided herein. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An isolated nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna, et al. (2003) *Nucleic Acids Res* 31 (13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw). To determine a "percent identity" between a query sequence and a subject sequence, the number of matching bases or amino acids in the alignment is divided by the total number of matched and mismatched bases or amino acids, followed by multiplying the result by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Recombinant constructs are also provided herein and can be used to transform plants or plant cells in order to modulate nitrogen levels. A recombinant nucleic acid construct comprises a nucleic acid encoding a nitrogen-modulating polypeptide as described herein, operably linked to a regulatory region suitable for expressing the nitrogen-modulating polypeptide in the plant or cell. Thus, a nucleic acid can comprise a nucleotide sequence that encodes any of the nitrogen-modulating polypeptides as set forth in SEQ ID NO:2, SEQ ID NOs:4-18, and the consensus sequence set forth in FIG. 1 (SEQ ID NOs:26-54).

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector"

is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., chlorsulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Regulatory Regions

The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to allow or facilitate transcription of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell* 1:977-984 (1989). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J.* 7, 4035-4044 (1988); Meier, et al., *Plant Cell*, 3, 309-316 (1991); and Zhang, et al., *Plant Physiology* 110: 1069-1079 (1996).

Examples of various classes of promoters are described below. Some of the promoters indicated below are described in more detail in U.S. patent application Ser. Nos. 60/505,689; 60/518,075; 60/544,771; 60/558,869; 60/583,691; 60/619,181; 60/637,140; 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species. Nucleotide sequences of promoters are set forth in SEQ ID NOs: 19-25.

Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO:19), YP0144 (SEQ ID NO:20), YP0190 (SEQ ID NO:21), p13879 (SEQ ID NO:22), YP0050 (SEQ ID NO:23), p32449 (SEQ ID NO:24), 21876 (SEQ ID NO:25), YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672 (SEQ ID NO:57), PT0678, PT0688, and PT0837 (SEQ ID NO:56) promoters, which drive transcription primarily in root tissue and to a lesser extent in ovules and/or seeds. Other examples of root-preferential promoters include the root-specific subdomains of the CaMV 35s promoter (Lam et at., *Proc. Natl. Acad. Sci. USA* 86:7890-7894 (1989)), root cell specific promoters reported by Conkling et al., *Plant Physiol.* 93:1203-1211 (1990), and the tobacco RD2 gene promoter.

Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et at., *Plant Cell* 1(9):839-853 (1989)), the soybean trypsin inhibitor promoter (Riggs et al., *Plant Cell* 1(6):609-621 (1989)), the ACP promoter (Baerson et al., *Plant Mol Biol*, 22(2):255-267 (1993)), the stearoyl-ACP desaturase gene (Slocombe et al., *Plant Physiol* 104(4): 167-176 (1994)), the soybean α' subunit of β-conglycinin promoter (Chen et al., *Proc Natl Acad Sci USA* 83:8560-8564 (1986)), the oleosin promoter (Hong et al., *Plant Mol Biol* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.* 13:5829-5842 (1993)), the beta-amylase gene promoter, and the barley hordein gene promoter. Other maturing endosperm promoters include the YP0092 (SEQ ID NO: 55), PT0676, and PT0708 promoters.

Ovary Tissue Promoters

Promoters that are active in ovary tissues such as the ovule wall and mesocarp can also be useful, e.g., a polygalacturonidase promoter, the banana TRX promoter, and the melon actin promoter.

Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0110, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654).

Photosynthetically Active Tissue Promoters

Photosynthetically active tissue promoters confer transcription in photosynthetically active tissue such as leaves and stems. Most suitable are promoters that drive expression only or predominantly such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.* 35:773-778 (1994)), the Cab-1 gene promoter from wheat (Fejes et al., *Plant Mol. Biol.* 15:921-932 (1990)), the CAB-1 promoter from spinach (Lubberstedt et al., *Plant Physiol.* 104:997-1006 (1994)), the cab1R promoter from rice (Luan et al., *Plant Cell* 4:971-981 (1992)), the pyruvate orthophosphate dikinase (PPDK) promoter from corn (Matsuoka et al., *Proc Natl Acad. Sci USA* 90:9586-9590 (1993)), the tobacco Lhcb1*2 promoter (Cerdan et al., *Plant Mol. Biol.* 33:245-255 (1997)), the *Arabidopsis thaliana* SUC2 sucrose-H+ symporter promoter (Truernit et al., *Planta* 196:564-570 (1995)), and thylakoid membrane protein promoters from spinach (psaD, psaF, psaE, PC, FNR, atpC, atpD, cab, rbcS).

Inducible Promoters

Inducible promoters confer transcription in response to external stimuli such as chemical agents or environmental stimuli. For example, inducible promoters can confer transcription in response to hormones such as giberellic acid or ethylene, or in response to light or drought.

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters

Other classes of promoters include, but are not limited to, leaf-preferential, stem/shoot-preferential, callus-preferential, and senescence-preferential promoters. Promoters designated YP0086, YP0188, YP0263, PT0758, PT0743, PT0829, YP0119, and YP0096, as described in the above-referenced patent applications, may also be useful.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, more than one regulatory region can be operably linked to the sequence of a polynucleotide encoding a carbon-modulating polypeptide.

Transgenic Plants and Plant Cells

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. Progeny include descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous nitrogen-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

Plant Species

The polynucleotides and vectors described herein can be used to transform a number of monocotyledonous and dicotyledonous plants and plant cell systems, including dicots such as alfalfa, amaranth, apple, beans (including kidney beans, lima beans, dry beans, green beans), broccoli, cabbage, carrot, castor bean, cherry, chick peas, chicory, clover, cocoa, coffee, cotton, crambe, flax, grape, grapefruit, lemon, lentils, lettuce, linseed, mango, melon (e.g., watermelon, cantaloupe), mustard, orange, peach, peanut, pear, peas, pepper, plum, potato, oilseed rape, rapeseed (high erucic acid and canola), safflower, sesame, soybean, spinach, strawberry, sugar beet, sunflower, sweet potatoes, tea, tomato, and yams, as well as monocots such as banana, barley, bluegrass, date palm, fescue, field corn, garlic, millet, oat, oil palm, onion, pineapple, popcorn, rice, rye, ryegrass, sorghum, sudangrass, sugarcane, sweet corn, switchgrass, timothy, and wheat. Brown seaweeds, green seaweeds, red seaweeds, and microalgae can also be used.

Thus, the methods and compositions described herein can be used with dicotyledonous plants belonging, for example, to the orders *Apiales, Arecales, Aristochiales, Asterales, Batales, Campanulales, Capparales, Caryophyllales, Casuarinales, Celastrales, Cornales, Cucurbitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticales,* and *Violales.* The methods and compositions described herein also can be utilized with monocotyledonous plants such as those belonging to the orders *Alismatales, Arales, Arecales, Asparagales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales,* and with plants belonging to *Gymnospermae,* e.g., *Cycadales, Ginkgoales, Gnetales,* and *Pinales.*

The methods and compositions can be used over a broad range of plant species, including species from the dicot genera *Amaranthus, Arachis, Brassica, Calendula, Camellia, Capsicum, Carthamus, Cicer, Cichorium, Cinnamomum, Citrus, Citrullus, Coffea, Crambe, Cucumis, Cucurbita, Daucus, Dioscorea, Fragaria, Glycine, Gossypium, Helianthus, Lactuca, Lens, Linum, Lycopersicon, Malus,*

*Mangifera, Medicago, Mentha, Nicotiana, Ocimum, Olea, Phaseolus, Pistacia, Pisum, Prunus, Pyrus, Rosmarinus, Salvia, Sesamum, Solanum, Spinacia, Theobroma, Thymus, Trifolium, Vaccinium, Vigna,* and *Vitis*; and the monocot genera *Allium, Ananas, Asparagus, Avena, Curcuma, Elaeis, Festuca, Hordeum, Lemna, Lolium, Musa, Oryza, Panicum, Pennisetum, Phleum, Poa, Saccharum, Secale, Sorghum, Triticosecale, Triticum,* and *Zea*.

The methods and compositions described herein also can be used with brown seaweeds, e.g., *Ascophyllum nodosum, Fucus vesiculosus, Fucus serratus, Himanthalia elongata,* and *Undaria pinnatifida*; red seaweeds, e.g., *Chondrus crispus, Cracilaria verrucosa, Porphyra umbilicalis,* and *Palmaria palmata*; green seaweeds, e.g., *Enteromorpha* spp. and *Ulva* spp.; and microalgae, e.g., *Spirulina* spp. (*S. platensis* and *S. maxima*) and *Odontella aurita*. In addition, the methods and compositions can be used with *Cryptheco-dinium cohnii, Schizochytrium* spp., and *Haematococcus pluvialis*.

In some embodiments, a plant is a member of the species *Ananus comosus, Brassica campestris, Brassica napus, Brassica oleracea, Glycine max, Gossypium* spp., *Lactuca sativa, Lycopersicon esculentum, Musa paradisiaca, Oryza sativa, Solanum tuberosum, Triticum aestivum, Vitis vinifera,* or *Zea mays*.

Methods of Inhibiting Expression of Nitrogen-Modulating Polypeptides

The polynucleotides and recombinant vectors described herein can be used to express or inhibit expression of a nitrogen-modulating polypeptide in a plant species of interest. The term "expression" refers to the process of converting genetic information of a polynucleotide into RNA through transcription, which is catalyzed by an enzyme, RNA polymerase, and into protein, through translation of mRNA on ribosomes. "Up-regulation" or "activation" refers to regulation that increases the production of expression products (mRNA, polypeptide, or both) relative to basal or native states, while "down-regulation" or "repression" refers to regulation that decreases production of expression products (mRNA, polypeptide, or both) relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a nitrogen-modulating polypeptide, e.g., SEQ ID NO:2, SEQ ID NOs:4-18, or the consensus sequence set forth in FIG. 1 (SEQ ID NOs: 26-54). A nucleic acid that decreases the level of a transcription or translation product of a gene encoding a nitrogen-modulating polypeptide is transcribed into an antisense nucleic acid similar or identical to the sense coding sequence of the nitrogen-modulating polypeptide. Alternatively, the transcription product of an isolated nucleic acid can be similar or identical to the sense coding sequence of a nitrogen-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254, 678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used: RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the nitrogen-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Transgenic Plant Phenotypes

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

Transgenic plants can have an altered phenotype as compared to a corresponding control plant that either lacks the transgene or does not express the transgene. A polypeptide can affect the phenotype of a plant (e.g., a transgenic plant) when expressed in the plant, e.g., at the appropriate time(s), in the appropriate tissue(s), or at the appropriate expression levels. Phenotypic effects can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

In some embodiments, a plant in which expression of a nitrogen-modulating polypeptide is modulated can have increased levels of seed nitrogen. For example, a nitrogen-modulating polypeptide described herein can be expressed in a transgenic plant, resulting in increased levels of seed nitrogen. The seed nitrogen level can be increased by at least 5 percent, e.g., 5, 10, 15, 20, 25, 30, 35, 40, 45, 50, 55, 60, 65, 70, 75, 80, 85, 90, 95, 100, or more than 100 percent, as compared to the seed nitrogen level in a corresponding control plant that does not express the transgene. In some embodiments, a plant in which expression of a nitrogen-modulating polypeptide is modulated can have decreased levels of seed nitrogen. The seed nitrogen level can be decreased by at least 5 percent, e.g., 5, 10, 15, 20, 25, 30, 35, 40, 45, 50, or more than 50 percent, as compared to the seed nitrogen level in a corresponding control plant that does not express the transgene.

Plants for which modulation of levels of seed nitrogen can be useful include, without limitation, alfalfa, lettuce, carrot, onion, broccoli, tomato, potato, sugarcane, grape, cotton, canola, sweet corn, popcorn, field corn, peas, beans, safflower, soybean, coffee, amaranth, rapeseed, peanut, sunflower, oil palm, wheat, rye, barley, oat, rice, millet, strawberry, pineapple, melon, peach, pear, apple, cherry, orange, lemon, grapefruit, plum, mango, banana, fescue, ryegrass, bluegrass, clover, timothy, sudangrass, switchgrass and sorghum. Increases in seed nitrogen in such plants can provide improved nutritional content in geographic locales where dietary intake of protein/amino acid is often insufficient. Decreases in seed nitrogen in such plants can be useful in situations where seeds are not the primary plant part that is harvested for human or animal consumption.

In some embodiments, a plant in which expression of a nitrogen-modulating polypeptide is modulated can have increased or decreased levels of nitrogen in one or more non-seed tissues, e.g., leaf tissues, stem tissues, root or corm tissues, or fruit tissues other than seed. For example, the nitrogen level can be increased by at least 5 percent, e.g., 5, 10, 15, 20, 25, 30, 35, 40, 45, 50, 55, 60, 65, 70, 75, 80, 85, 90, 95, 100, or more than 100 percent, as compared to the nitrogen level in a corresponding control plant that does not express the transgene. In some embodiments, a plant in which expression of a nitrogen-modulating polypeptide is modulated can have decreased levels of nitrogen in one or more non-seed tissues. The nitrogen level can be decreased by at least 5 percent, e.g., 5, 10, 15, 20, 25, 30, 35, 40, 45, 50, or more than 50 percent, as compared to the nitrogen level in a corresponding control plant that does not express the transgene.

Plants for which modulation of levels of nitrogen in non-seed tissues can be useful include, without limitation, alfalfa, lettuce, carrot, onion, broccoli, tomato, potato, sugarcane, grape, sweet corn, popcorn, field corn, peas, beans, safflower, soybean, coffee, amaranth, rapeseed, peanut, sunflower, oil palm, wheat, rye, barley, oat, rice, millet, strawberry, pineapple, melon, peach, pear, apple, cherry, orange, lemon, grapefruit, plum, mango, banana, fescue, ryegrass, bluegrass, clover, timothy, sudangrass, switchgrass and sorghum.

Increases in non-seed nitrogen in such plants can provide improved nutritional content in edible fruits and vegetables, or improved animal forage. Decreases in non-seed nitrogen can provide more efficient partitioning of nitrogen to plant part(s) that are harvested for human or animal consumption.

Typically, a difference (e.g., an increase) in the amount of nitrogen in a transgenic plant or cell relative to a control plant or cell is considered statistically significant at $p<0.05$ with an appropriate parametric or non-parametric statistic, e.g., Chi-square test, Student's t-test, Mann-Whitney test, or F-test. In some embodiments, a difference in the amount of nitrogen is statistically significant at $p<0.01$, $p<0.005$, or $p<0.001$. A statistically significant difference in, for example, the amount of nitrogen in seeds of a transgenic plant compared to the amount in cells of a control plant indicates that (1) the recombinant nucleic acid present in the transgenic plant results in altered nitrogen levels and/or (2) the recombinant nucleic acid warrants further study as a candidate for altering the amount of nitrogen in a plant.

Articles of Manufacture

Also provided herein are articles of manufacture that can include, for example, a mixture of seeds (e.g., a substantially uniform mixture of seeds) from the transgenic plants provided herein. The seed mixture can be conditioned and packaged using means known in the art to prepare an article of manufacture. A package of seed can have a label e.g., a tag or label secured to the packaging material, a label printed on the packaging material or a label inserted within the package. The label can indicate that plants grown from the seeds contained within the package can produce a crop having a higher level of seed nitrogen relative to corresponding control plants.

The invention will be further described in the following examples, which do not limit the scope of the invention described in the claims.

EXAMPLES

Example 1—Transgenic Plants

The following symbols are used in the Examples: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following nucleic acids were isolated from *Arabidopsis thaliana* ecotype Wassilewskija (Ws) plants. Ceres cDNA ID 2998984 is a genomic DNA clone that is predicted to encode a 505 amino acid (SEQ ID NO:2) putative oligopeptide transporter polypeptide. Ceres clone 117581 (cDNA ID 23364185; SEQ ID NO:3) is a cDNA clone that is predicted to encode a 587 amino acid (SEQ ID NO:4) putative peptide transporter polypeptide.

Each isolated polynucleotide described above was cloned into a vector containing a phosphinothricin acetyltransferase gene, which confers Finale™ resistance to transformed plants. NB42-35S binary vectors were constructed that contained Ceres cDNA ID 2998984 or Ceres clone 117581 operably linked to the cauliflower mosaic virus (CaMV) 35S regulatory region. The NB42-35S binary vector is a derivative of the pMOG800 binary vector.

Wild-type *Arabidopsis thaliana* ecotype C24 plants were transformed separately with each NB42-35S binary vector containing Ceres cDNA ID 2998984 or Ceres clone 117581. The transformations were performed essentially as described in Bechtold et al., *C.R. Acad. Sci. Paris*, 316: 1194-1199 (1993).

Transgenic *Arabidopsis* lines containing Ceres cDNA ID 2998984 or Ceres clone 117581 were designated SR00829 and SR05001, respectively. The presence of the Ceres cDNA ID 2998984 vector in SR00829 and the Ceres clone 117581 vector in SR05001 was confirmed by Finale™ resistance, polymerase chain reaction (PCR) amplification from green leaf tissue extract, and sequencing of PCR products. As controls for transgenic *Arabidopsis* ecotype C24 plants, wild-type *Arabidopsis* ecotype C24 plants were transformed with the empty vector NB42-35S.

The in planta nucleotide sequences of Ceres cDNA ID 2998984 and Ceres clone 117581 were compared to the homologous *Arabidopsis* ecotype Columbia sequences. The in planta nucleotide sequence of Ceres clone 117581 differed from the homologous Columbia sequence by one nucleotide. The in planta nucleotide sequence of Ceres cDNA ID 2998984 contained base pair insertions, deletions, and substitutions compared to the homologous Columbia sequence (SEQ ID NO:1).

To determine if the overall structure of the predicted polypeptide encoded by Ceres cDNA ID 2998984 was similar to that of the predicted polypeptide encoded by the homologous Columbia nucleotide sequence (SEQ ID NO:1), both sequences were analyzed for potential transmembrane domains characteristic of transporter polypeptides using the TMpred program (ch.embnet.org/software/TMPRED_form). The analysis indicated that both predicted polypeptides had the expected 12 transmembrane spanning regions. However, prediction of the translation initiation sites indicated that the predicted polypeptide encoded by Ceres cDNA ID 2998984 was 40 amino acids shorter at the amino terminus than the predicted polypeptide encoded by the Columbia homolog. Therefore, the predicted polypeptide encoded by Ceres cDNA ID 2998984 lacked the secretory signal peptide sequence contained in the first 40 amino acids of the predicted Columbia polypeptide sequence according to the SignalP algorithm (cbs.dtu.dk/services/SignalP/). Analysis of the predicted polypeptide sequence encoded by Ceres cDNA ID 2998984 using the iPSORT signal sequence prediction algorithm (hc.ims.u-tokyo.ac.jp/iPSORT/index.html#aaindex) indicated that the first 40 amino acids contained a potential chloroplast targeting signal sequence.

Transgenic *Arabidopsis* lines were screened as follows: 1) $T_1$ candidates in the greenhouse were screened for morphological phenotypes, 2) $T_2$ seeds were analyzed for carbon and nitrogen content, 3) increased carbon and/or nitrogen content was confirmed in $T_3$ seeds, and 4) $T_2$ plants were evaluated for negative phenotypes and Finale™ segregation.

Five events of each of SR00829 and SR05001 were screened for visible phenotypic alterations in the $T_1$ generation. The physical appearance of all of the $T_1$ plants was identical to that of the corresponding control plants.

Example 2—Analysis of Carbon and Nitrogen Content in Transgenic *Arabidopsis* Seeds Approximately 2.00±0.15 mg of dried transgenic *Arabidopsis* seeds (about 100 seeds) were weighed into a tin cup and analyzed for total carbon and nitrogen content. Three matched controls were prepared in a manner identical to the experimental samples and spaced evenly throughout the batch. The first three samples in every batch were a blank (empty tin cup), bypass, (approximately 5 mg of aspartic acid), and a standard (5.00±0.15 mg aspartic acid), respectively. Aspartic acid was weighed into a tin cup using an analytical balance. Blanks were entered between every 15 experimental samples.

Analysis was completed using a FlashEA 1112 NC Analyzer (Thermo Finnigan, San Jose, Calif.). The instrument parameters were as follows: left furnace 900° C., right furnace 840° C., oven 50° C., gas flow carrier 130 mL/min., and gas flow reference 100 mL/min. The data parameter LLOD was 0.25 mg for the standard and different for other materials. The data parameter LLOQ was 3 mg for the standard, 1 mg for seed tissue, and different for other materials.

Quantification was performed using EA 1112 software. The results were normalized and expressed in absolute percentages. Each sample was analyzed in triplicate, and the standard deviation was calculated. Non-transgenic controls were previously determined to have a total carbon content of 53.3±2.4% and a total nitrogen content of 3.9±0.3%. The deviation from theoretical of the aspartic acid standard was ±2.0% for carbon and ±1.0% for nitrogen. To be declared valid, each run was required to have an aspartic acid (standard) weight of 5 mg±0.15 mg, and the blank(s) were required to have no recorded nitrogen or carbon content. The percent standard deviation between replicate samples was required to be below 10%.

Example 3—Results for SR00829 Events $T_2$ and $T_3$ seeds from two events of SR00829 containing Ceres cDNA ID 2998984 were analyzed for total carbon and nitrogen content as described in Example 2.

The nitrogen content of $T_2$ seeds from two events of SR00829 was significantly increased compared to the nitrogen content of corresponding control seeds. As presented in Table 1, the nitrogen content was increased to 110% and 109% in seeds from events −01 and −02, respectively, compared to the nitrogen content in control seeds.

TABLE 1

Total nitrogen content (% control)
of $T_2$ and $T_3$ seeds from SR00829 events

|  | Event-01 | Event-02 | Control |
|---|---|---|---|
| $T_2$ | 110 ± 1 | 109 ± 2 | 100 ± 1 |
| p-value | 0.001 | 0.002 | NA |
| $T_3$ | 111 ± 3 | 118 ± 5 | 100 ± 3 |
| p-value | <0.01 | 0.01 | NA |

The nitrogen content of $T_3$ seeds from two events of SR00829 was significantly increased compared to the nitrogen content of corresponding control seeds. As presented in Table 1, the nitrogen content was increased to 111% and 118% in seeds from events −01 and −02, respectively, compared to the nitrogen content in control seeds.

The carbon content of $T_2$ and $T_3$ seeds from SR00829 events was not observed to differ significantly from the carbon content of corresponding control seeds.

$T_3$ seeds from SR00829 events analyzed for carbon and nitrogen content were collected from one $T_2$ plant from each event.

The segregation of Finale™ resistance in $T_2$ plants from events −01 and −02 of SR00829 was a 3:1 ratio of resistant to sensitive.

There were no observable or statistically significant differences between $T_2$ SR00829 and control plants in germination, onset of flowering, rosette area, fertility, plant height, and general morphology/architecture.

Example 4—Results for SR05001 Events $T_2$ and $T_3$ seeds from two events of SR05001 containing Ceres clone 117581 were analyzed for total carbon and nitrogen content as described in Example 2.

The carbon content of $T_2$ seeds from one event of SR05001 was significantly decreased compared to the carbon content of corresponding control seeds. As presented in Table 2, the carbon content was decreased to 97% in seeds from event −02 compared to the carbon content in control seeds.

TABLE 2

Total carbon content (% control) of $T_2$ and $T_3$ seeds from SR05001 events

|  | Event-02 | Event-03 | Control |
|---|---|---|---|
| $T_2$ | 97 ± 2 | 102 ± 2 | 100 ± 1 |
| p-value | 0.03 | 0.14 | NA |
| $T_3$ | 106 ± 1 | 107 ± 2 | 100 ± 2 |
| p-value | 0.01 | 0.01 | NA |

The nitrogen content of $T_2$ seeds from two events of SR05001 was significantly increased compared to the nitrogen content of corresponding control seeds. As presented in Table 3, the nitrogen content was increased to 112% and 115% in seeds from events −02 and −03, respectively, compared to the nitrogen content in control seeds.

TABLE 3

Total nitrogen content (% control)
of $T_2$ and $T_3$ seeds from SR05001 events

|  | Event-02 | Event-03 | Control |
|---|---|---|---|
| $T_2$ | 112 ± 3 | 115 ± 1 | 100 ± 4 |
| p-value | <0.01 | <0.01 | NA |
| $T_3$ | 109 ± 1 | 106 ± 2 | 100 ± 2 |
| p-value | <0.01 | 0.02 | NA |

The carbon content of $T_3$ seeds from two events of SR05001 was significantly increased compared to the carbon content of corresponding control seeds. As presented in Table 2, the carbon content was increased to 106% and 107% in seeds from events −02 and −03, respectively, compared to the carbon content in control seeds.

The nitrogen content of $T_3$ seeds from two events of SR05001 was significantly increased compared to the nitrogen content of corresponding control seeds. As presented in Table 3, the nitrogen content was increased to 109% and 106% in seeds from events −02 and −03, respectively, compared to the nitrogen content in control seeds.

$T_3$ seeds from SR05001 events analyzed for carbon and nitrogen content were collected from one $T_2$ plant from each event.

The segregation of Finale™ resistance in $T_2$ plants from events −02 and −03 of SR05001 was a 3:1 ratio of resistant to sensitive.

There were no observable or statistically significant differences between $T_2$ SR05001 and control plants in germination, onset of flowering, rosette area, fertility, seed size, and general morphology/architecture.

Example 5—Determination of Functional Homolog and/or Ortholog Sequences

A subject sequence was considered a functional homolog or ortholog of a query sequence if the subject and query sequences encoded proteins having a similar function and/or activity. A process known as Reciprocal BLAST (Rivera et al., *Proc. Natl. Acad. Sci. USA*, 95:6239-6244 (1998)) was used to identify potential functional homolog and/or ortholog sequences from databases consisting of all available public and proprietary peptide sequences, including NR from NCBI and peptide translations from Ceres clones.

Before starting a Reciprocal BLAST process, a specific query polypeptide was searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides were designated as a cluster.

The main Reciprocal BLAST process consists of two rounds of BLAST searches; forward search and reverse search. In the forward search step, a query polypeptide sequence, "polypeptide A," from source species SA was BLASTed against all protein sequences from a species of interest. Top hits were determined using an E-value cutoff of 10-5 and an identity cutoff of 35%. Among the top hits, the sequence having the lowest E-value was designated as the best hit, and considered a potential functional homolog or ortholog. Any other top hit that had a sequence identity of 80% or greater to the best hit or to the original query polypeptide was considered a potential functional homolog or ortholog as well. This process was repeated for all species of interest. In the reverse search round, the top hits identified in the forward search from all species were BLASTed against all protein sequences from the source species SA. A top hit from the forward search that returned a polypeptide from the aforementioned cluster as its best hit was also considered as a potential functional homolog or ortholog.

Functional homologs and/or orthologs were identified by manual inspection of potential functional homolog and/or ortholog sequences. Representative functional orthologs for SEQ ID NO:4 are shown in FIG. 1. The percent identities of functional orthologs to SEQ ID NO:4 are shown below in Table 4.

TABLE 4

Percent identity to Ceres clone 117581 (SEQ ID NO: 4)

| Designation | Species | SEQ ID NO: | % Identity | e-value |
|---|---|---|---|---|
| CeresClone: 328378 | *Zea mays* | 5 | 70.4 | 0 |
| gi|2655098 | *Hordeum vulgare* subsp. *vulgare* | 6 | 68.2 | 0 |
| gi|34895718 | *Oryza sativa* subsp. *japonica* | 7 | 68 | 0 |
| gi|50933627 | *Oryza sativa* subsp. *japonica* | 8 | 64 | 0 |
| gi|4102839 | *Lycopersicon esculentum* | 9 | 63 | 0 |
| gi|31088360 | *Vicia faba* | 10 | 62.9 | 0 |
| gi|6635838 | *Prunus dulcis* | 11 | 61.4 | 0 |
| gi|56784523 | *Oryza sativa* subsp. *japonica* | 12 | 56.7 | 0 |
| gi|56784524 | *Oryza sativa* subsp. *japonica* | 13 | 51.6 | 0 |
| gi|6409176 | *Oryza sativa* | 15 | 49.5 | 0 |
| gi|50059161 | *Triticum aestivum* | 14 | 49.5 | 0 |
| CeresClone: 352232 | *Zea mays* | 16 | 48.5 | 0 |
| gi|33411520 | *Prunus persica* | 17 | 47.1 | 0 |
| gi|31429847 | *Oryza sativa* | 18 | 47.1 | 0 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing the level of nitrogen in a plant, said method comprising transforming a plant cell with an exogenous nucleic acid comprising a nucleotide sequence encoding a polypeptide having 95% percent or greater sequence identity to the amino acid sequence set forth in SEQ ID NO:2, and regenerating said plant from said transformed plant cell, wherein expression of said nucleotide sequence increases the level of nitrogen in said transformed plant as compared to the level of nitrogen in a control plant of the same species which is not transformed with said exogenous nucleic acid.

2. The method of claim 1, wherein said exogenous nucleic acid is operably linked to a regulatory region.

3. The method of claim 2, wherein said regulatory region is a promoter selected from the group consisting of YP0092 having SEQ ID NO:55, PT0672 having SEQ ID NO:57, PT0837 having SEQ ID NO:56, a napin promoter, an Arcelin-5 promoter, a phaseolin gene promoter, a soybean trypsin inhibitor promoter, an ACP promoter, a stearoyl-ACP desaturase gene promoter, a soybean subunit of β-conglycinin promoter, an oleosin promoter, a 15 kD zein promoter, a 16 kD zein promoter, a 19 kD zein promoter, a 22 kD zein promoter, a 27 kD zein promoter, an Osgt-1 (*Oryza sativa* glutelin-1) promoter, a beta-amylase gene promoter, and a barley hordein gene promoter.

4. A method of producing a plant tissue, said method comprising growing a plant comprising an exogenous nucleic acid comprising a nucleotide sequence encoding a polypeptide having 95% percent or greater sequence identity to the amino acid sequence set forth in SEQ ID NO:2, wherein said plant expressing said nucleotide sequence has an increased level of nitrogen as compared to the level of nitrogen in a control plant of the same species which lacks said exogenous nucleic acid; and obtaining tissue from said plant.

5. A transformed plant cell comprising an exogenous nucleic acid comprising a nucleotide sequence encoding a polypeptide having 95% percent or greater sequence identity to the amino acid sequence set forth in SEQ ID NO:2, wherein expression of the nucleotide sequence increases the level of nitrogen in the transformed plant cell as compared to the level of nitrogen of a cell of a control plant of the same species which is not transformed with said exogenous nucleic acid.

6. A transgenic plant comprising the plant cell of claim 5.

7. A progeny of the plant of claim 6, wherein said progeny expressing said nucleotide sequence has an increased level of nitrogen as compared to the level of nitrogen in a control plant of the same species which is not transformed with said exogenous nucleic acid.

8. A seed from the transgenic plant according to claim 6, wherein said seed comprises said nucleic acid.

9. A vegetative tissue from the transgenic plant according to claim 6; wherein said vegetative tissue comprises said nucleic acid.

10. The method of claim 1, wherein said nucleotide sequence encodes a polypeptide comprising the amino acid sequence set forth in SEQ ID NO:2.

11. The method of claim 1, wherein said plant is a member of the genus *Brassica, Glycine, Gossypium, Oryza, Panicum,* or *Zea*.

12. The method of claim 4, wherein said nucleotide sequence encodes a polypeptide comprising the amino acid sequence set forth in SEQ ID NO:2.

13. The method of claim 4, wherein said plant tissue is a member of the genus *Brassica, Glycine, Gossypium, Oryza, Panicum,* or *Zea*.

14. The method of claim 5, wherein said nucleotide sequence encodes a polypeptide comprising the amino acid sequence set forth in SEQ ID NO:2.

15. The method of claim 5, wherein said plant is a member of the genus *Brassica, Glycine, Gossypium, Oryza, Panicum,* or *Zea*.

* * * * *